United States Patent
Kloepfer et al.

(10) Patent No.: US 7,901,364 B2
(45) Date of Patent: *Mar. 8, 2011

(54) CONSOLIDATED BODY FLUID TESTING DEVICE AND METHOD

(75) Inventors: Hans G. Kloepfer, Noblesville, IN (US); Reinhard Hafellner, St. Margarethen (AT); Charles W. Roach, Richmond Heights, MO (US); Charles Thomeczek, Fishers, IN (US)

(73) Assignee: Micronix, Inc, Carmel, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/030,441

(22) Filed: Jan. 5, 2005

(65) Prior Publication Data

US 2005/0177072 A1    Aug. 11, 2005

Related U.S. Application Data

(63) Continuation of application No. 10/313,331, filed on Dec. 6, 2002, now Pat. No. 6,840,912.

(60) Provisional application No. 60/340,442, filed on Dec. 7, 2001.

(51) Int. Cl.
*A61B 5/00* (2006.01)

(52) U.S. Cl. .......................... 600/583; 606/181; 600/584

(58) Field of Classification Search .................. 600/573, 600/576, 583, 584; 606/181–183
See application file for complete search history.

(56) References Cited

U.S. PATENT DOCUMENTS

| | | | | |
|---|---|---|---|---|
| 4,243,035 A | * | 1/1981 | Barrett | 604/1 |
| 4,799,926 A | * | 1/1989 | Haber | 604/187 |
| 4,995,402 A | * | 2/1991 | Smith et al. | 600/584 |
| 5,047,044 A | | 9/1991 | Smith et al. | |
| 5,108,889 A | * | 4/1992 | Smith et al. | 435/4 |
| 5,318,584 A | * | 6/1994 | Lange et al. | 606/182 |
| 5,730,753 A | | 3/1998 | Morita | |
| 5,800,779 A | * | 9/1998 | Johnson | 422/58 |
| 5,871,494 A | | 2/1999 | Simons et al. | |
| 5,947,957 A | | 9/1999 | Morris | |
| 5,971,941 A | * | 10/1999 | Simons et al. | 600/573 |
| 6,093,156 A | | 7/2000 | Cunningham et al. | |
| 6,099,484 A | | 8/2000 | Douglas et al. | |
| 6,143,164 A | * | 11/2000 | Heller et al. | 600/583 |
| 6,155,992 A | * | 12/2000 | Henning et al. | 600/583 |
| 6,261,245 B1 | | 7/2001 | Kawai et al. | |
| 6,315,738 B1 | * | 11/2001 | Nishikawa et al. | 600/583 |

(Continued)

OTHER PUBLICATIONS

TheraSense FreeStyle, Blood glucose monitoring system, TheraSense, 1360 South Loop Road, Alameda, CA 94502, Screen print from (www.childrenwithdiabetes.com/d 0i 280.htm) (2005).

(Continued)

*Primary Examiner* — Max Hindenburg
*Assistant Examiner* — Michael C Stout
(74) *Attorney, Agent, or Firm* — E. Victor Indiano; Indiano Law Group

(57) ABSTRACT

A body fluid testing device includes a body member and a tissue penetrator carried by the body member. A test strip holder is carried by the body member, and a test strip is carried by the test strip holder. The test strip is capable of receiving a body fluid thereon and processing the body fluid into a form suitable for yielding test results relating to the content of the body fluid. The body member, tissue penetrator, test strip holder and test strip are designed for a single use and for disposal as a unit without disassembly.

21 Claims, 13 Drawing Sheets

U.S. PATENT DOCUMENTS

| | | | |
|---|---|---|---|
| 6,332,871 | B1 | 12/2001 | Douglas et al. |
| 6,338,720 | B1 | 1/2002 | Morikawa et al. |
| 6,419,661 | B1 | 7/2002 | Kuhr et al. |
| 6,468,287 | B1 | 10/2002 | Baugh |
| 6,485,439 | B1 | 11/2002 | Roe et al. |
| 6,840,912 | B2* | 1/2005 | Kloepfer et al. ............... 600/583 |
| 6,866,675 | B2* | 3/2005 | Perez et al. .................. 606/181 |
| 7,299,081 | B2* | 11/2007 | Mace et al. .................... 600/345 |
| 2001/0027328 | A1* | 10/2001 | Lum et al. ..................... 606/186 |
| 2002/0052618 | A1* | 5/2002 | Haar et al. .................... 606/181 |
| 2002/0169393 | A1* | 11/2002 | Cunningham et al. ........ 600/573 |
| 2004/0102715 | A1* | 5/2004 | Latterell et al. ............... 600/576 |
| 2005/0149090 | A1* | 7/2005 | Morita et al. .................. 606/181 |

OTHER PUBLICATIONS

Accu-Chek Complete, advanced data management meter, Roche Diagnostics Corporation, 9115 Hague Road, Indianapolis, IN 46250, Screen print from (www.childrenwithdiabetes.com/d_0i_240.htm) (2005).

ReliOn Monitor, affordable blood glucose testing system, ReliOn, 338 Main Street, Chester, NJ 07930, Screen print from www/childrenwithdiabetes.com/d_0i_300.htm (2005).

Precision Xtra, meter for testing for bllod glucose and blood ketones, MediSense, Inc., An Abbott Laboratories Company, 4A Crosby Drive, Bedford, MA 01730 Screen print from (www.childrenwithdiabetes.com/d_0i_191.htm) (2005).

One Touch® Ultra, blood glucose meter with results in five seconds, LifeScan Inc., 1000 Gibraltar Drive, Milpitas, CA 95035-6314 Screen print from (www.childrenwithdiabetes.com/d_0i_290.htm) (2005).

Diabetic Express, The Diabetes Superstore!, p. 1-4, Screen print from (www.childrenwithdiabetes.com/d_0i_000.htm) (2005).

Bayer Care, products and services for diabetics, pp. 1-2 Screen print from (www.bayercarediabetes.com/prodserv/products/glueEliteXL/index.asp) (2005).

Focus Plus, Blood Glucose Monitoring System, QuestStar Medical, Inc., 10180 Viking Drive, Eden Prairie, MN 55344, pp. 1-2 Screen print from (www.queststannedical.com/) (2005).

Terumo, products for people with diabetes, Terumo Corporation, Japan, Screen print from (www.terumo.co.jp/English/products/products_09.html) (2005).

GlucoWatch, Automatic Glucose Biographer, Cygnus, Inc.,400 Penobscot, Drive, Redwood, CA 94063, pp. 1-2b Screen print from www.glucowatch.com(2005).

* cited by examiner

CONSOLIDATED BODY FLUID TESTING DEVICE AND METHOD

CLAIM OF PRIORITY

The instant application is a continuation of Kloepfer et al U.S. patent application Ser. No. 10/313,331, filed on 6 Dec. 2002; which, on 11 Jan. 2005 issued as U.S. Pat. No. 6,840,912; and claims priority to Kloepfer, Kloepfer and Roach, U.S. Provisional Patent Application No. 60/340,442 filed 7 Dec. 2001, both of which are hereby expressly incorporated by reference.

GOVERNMENT INTEREST STATEMENT

This invention was made with Government support under grant number R44 DK59219 from the National Institutes of Health. The Government has certain rights to this invention.

TECHNICAL FIELD OF THE INVENTION

The present invention relates to methods and devices for testing analysis fluids, and more particularly to a consolidated testing apparatus for use in performing analyses of one or more components of a fluid. Significant contemplated applications of the invention are in the biological sciences, especially diagnostic medicine. In this field, analysis fluids would primarily be bodily fluids, notably whole blood.

BACKGROUND OF THE INVENTION

A. Overview of Disease Conditions Warranting a Need for the Present Invention Diabetes has been referred to as the "undiagnosed epidemic of the third millennium". Some experts predict the number of diabetics world-wide to triple over the next 15 years to about 320 million. Self-monitoring of blood glucose (SMBG) is considered the quintessential prerequisite for diabetes management and treatment. As will be explained in more detail, most current SMBG systems, whether designed for patient or professional use, still have significant limitations.

Diabetes has reached alarming proportions in the western world and is growing at epidemic rates in countries other than the western world. Strategies for diagnosis and care are well developed (though still sub-optimal) in the western world, but marginal in developing countries.

The three major types of diabetes are type 1 (formerly insulin-dependent diabetes mellitus, IDDM, juvenile-onset), type 2 (formerly non-insulin-dependent diabetes mellitus, NIDDM, adult-onset), and gestational diabetes. About 130,000 children in the US have type 1 diabetes. Treatment for type 1 consists of insulin injections, diet and exercise.

In type 2 diabetes, treatment may include insulin, but preferably oral glucose lowering agents, diet, weight reduction and exercise. Approximately ninety percent (90%) of diabetics are type 2.

Powerful drivers for rising prevalence of diabetes and impaired glucose tolerance (IGT) in the US are growing minority populations, along with the graying, and the fattening of America. The yearly death toll from diabetes is one half million. Diabetics are predisposed to heart disease, peripheral vascular disease, stroke, retinopathy, kidney disease and neuropathy. The latter is associated with amputations, silent myocardial infarction and sudden death, and it accounts for over 300,000 hospitalizations each year. The number of annual hospital days is 6 million and emergency room visits close to 600,000.

Direct costs in 1992 were estimated at $39.1 billion for institutional and $6.2 billion for outpatient care. Today's total diabetes-related toll to the US economy (direct and indirect costs combined) is estimated to approach $150 billion.

As a true cure for diabetes remains elusive, tight glucose control will continue to be the sine-qua-non of diabetes combat strategies. The benefits of tight glucose control in curbing diabetes-related complications are now authoritatively documented. This evidence also suggests that a large portion of type 2 diabetics may benefit from tight glucose control and insulin. As worldwide knowledge about diabetes will be nurtured by the information age and media-assisted education, masses of undiagnosed diabetics who would benefit from tight glucose control will eventually be brought into the system. Since testing technology will also further mature, these megatrends will co-functionally establish an enormous market for SMBG in the future.

B. Discussion of Prior Art Products and Techniques

The mainstay of treatment for type 1 and many type 2 diabetics is SMBG in concert with responding self-administration of insulin to harmonize glucose levels. Current SMBG systems are typically comprised of a test strip-type, dry chemistry device; The test strip is insertable into a hand-held meter that contains a display that gives the user a read-out of results. Alternately, results can be obtained by comparing reaction colors to printed color charts. The combined 1998 world market for teststrips, meters and auxiliary products (lancets, sticking devices, swabs, etc.) was $3 billion and is now in excess of $4 billion, with $2 billion in the US alone. Long term growth projections for the market are 12-15% per annum.

Approximately two thirds (⅔) of the market is in teststrips. Examples of known test strip and meter systems are those sold by Beyer Diagnostics; Cascade Medical; LXN Corporation; LifeScan; MediSense; ReliOn; Roche Diagnostics; Terumo Corporation and TheraSense.

From a provider perspective, the main shortfall is that current systems are generally limited to the measurement of glucose. This is in drastic discord with the concept of diabetes as a multi-factorial metabolic syndrome. From a user point of view, there are still limitations in those features that consumers and users believe to be important, such as (1) minimal invasiveness; (2) speed of analysis and (3) ease of performance and minimal complexity (inconvenience) from primary and auxiliary product mixes.

The vast majority of current SMBG systems utilize more or less "invasive" technology as they require that finger tips be lanced to cause bleeding, which is the source of blood used in the test. Most current devices require the finger to be lanced to obtain blood samples in a range between 2 and 30 ml. Non-invasive and minimally invasive technologies (such as the one of the instant invention) have been under active development for years, but made it to market only on a very limited scale due to technical difficulties.

1. Invasive Systems. Several dry-chemistry technologies exist for testing of whole blood specimens. In most devices liquid reagents are applied onto solid support substrates by some impregnation or coating method. After solvent evaporation, the dry and therefore stable reagent is contained within a reactive zone or signal member (test field). As the blood sample makes contact with the reagents on a test strip, a chemical reaction is initiated with the analyte to be measured.

Both photometric and electro-sensimetric detection principles are in use for measuring compounds of interest in the reagent-reacted analyte on the test strip. Most systems employ reflectance photometry. In these meters, light of a wavelength absorbed by the colored reaction product is shined onto the surface of the test field and the reflected portion of the light is monitored. In contrast to conventional photometry where absorbance is measured from reduced light transmittance in the direction of the incident beam, reflectance is measured at locations angled away from incident light. As light of varying wavelengths is reflected in different directions, an informed choice must be made as to which incident and reflective angles to select for obtaining a signal that is most sensitively and most specifically related to concentration.

Preferably, the photocurrent detector (photodiode) of the metering device is positioned at a location where unspecific scattering is minimal, and specific reflectance is maximized. However, since the two can usually not be completely spatially separated, pure signals are by definition unobtainable.

An advantage of photometric systems is that they measure color. Potentially, this enables both visual and instrumented signal recognition. Visual interpretation can serve as a confidence check for quantitative results provided by the meter. Importantly, in markets where meters are not readily available, glucose concentration can still be determined semi-quantitatively by a visual comparison of reaction colors on the test strip to standardized color charts.

Unfortunately, the important feature of visual backup is realized only in a minority of present systems. This limitation resides in the method by which cellular component of blood is separated from plasma. In older products plasma was separated by soak through methods into coated bibulous materials or reagent films. Cells were then manually removed from the site of blood application by either washing or wiping them away, potentially giving rise to significant operator-induced errors.

Several newer methods permit separation by means other than washing or wiping. The most frequently used methods are separation by porous glass fiber fleeces or membranes. In these matrices pore sizes are chosen so that cellular component is held back within the matrix, whereas plasma diffuses through the separating and into the detection layer.

2. Non-Invasive (NI) and Semi-Invasive Technology. The dream goal for the SMBG market of a completely non-invasive glucose monitoring technology, although pursued for over a decade, has so far proven elusive, despite perennial promises from companies in the industry. These failures have led to predictions that completely non-invasive optical technology (infrared or other) may not make it to market in any significant way, for both cost and technical reasons. It is also argued that this lack of success was predictable from early theoretical considerations of signal engineering. These considerations include the numerous and variable challenges of isolating a meaningful signal against a background of overpowering non-specific noise, such as noise from water. An authoritative recent review of NI glucose testing technology concludes that: " . . . none of the NI experiments reviewed provides proof that the signal is related to actual blood glucose concentration. Clark error grid presentation shows performance that is not acceptable for home glucose meters."

A promising alternative to non-invasive is "semi-invasive" or minimally invasive testing using interstitial fluid (IF). The only product currently marketed that employs this technology is Glucowatch™ from Cygnus, Inc. It uses electrically stimulated (reverse iontophoresis) glucose extraction from IF into a sensor-equipped sample pad. The product was recently approved by the FDA but only for supplementary (trend) testing. Reported problems with IF sampling are variations in skin thickness and permeability, changes in blood/IF equilibration, sweating, signal instability and skin irritation. Furthermore, the watch must be recalibrated every 12 hrs. which is done by invasive finger stick measurements.

In the future the SMBG market will increasingly be driven by consumer demand, managed care, and cost pressures from third party reimbursement companies. In this environment a market conversion from established and affordable invasive whole blood technology to unproven and costly non-invasive systems appears unlikely. However, it is expected that the market will migrate to invasive systems which minimize invasiveness and its associated pain. As such, the Applicant's minimally invasive and relatively less painful technology is believed by Applicants to better achieve the goals sought by the industry, and be well placed in the direction in which the market is heading.

C. The Present Invention Strives to Improve over the Known Prior Art

One development goal is to remove, or at least decrease the pain associated with finger sticks and reduce the complexity of test performance by reducing the number of separate components required to perform a blood test.

An inventive feature of the Applicant's invention is the consolidation of the test procedure components with the exception of the meter, into one single disposable test strip device. The product "clutter" of the prior art non-meter components including test strips, meters, lancets, lancet shooting devices, alcohol bottles or sealed swabs, multiple vials and bags requires the user to assemble and spread out a multitude of separate components on a flat surface such as a table or counter top, before testing can even begin. It is a perceived burden by users, and a deterrent for many diabetics to perform SMBG at all. The Applicants' innovative concept of sweeping consolidation of a multitude of components into one single disposable of lancing site preparation, painless lancing (tiny sample, e.g. forearm), dosing and non-instrumented monitoring should reduce perceived inconvenience to the absolute minimum, making testing easier and widely accessible to the public. In instrument monitored versions, the monitor (meter) will comprise a second component.

The technology has four (4) contributive components: (1) unitization of lancing site preparation, lancing, dosing and testing; (2) direct (filter-less) absorption of blood plasma into polymer-based reagent films; (3) removal of cellular component by capillary force; and (4) visual recognition of designated glucose cut-points by the novel threshold assay (redox titration on a test strip) principle (in non-instrumented versions). In this mode of operation, only a single polymeric film with a thickness in the micrometer range (<50 m dry film) is required for instant accommodation of both plasma acquisition and chemical analysis. Feasibility in theory and experiment for the candidate technological principles has been demonstrated by Applicants.

Elements of the consolidated testing device of the present invention are: (1) incorporation of a lancet into a test strip containing device at a side opposite to blood entry capillary with that side becoming the (currently separated) lancet/plastic support unit; (2) incorporation of an antiseptic cleaning swab into the lancet cap and (3) incorporation of a pressure cup into the lancet cap lid for focused acquisition of miniature blood specimens by enhancing blood flow from tissue site that, under normal conditions do not yield sufficient blood for testing purposes.

These steps eliminate product clutter by obviating separate vials, swabs, lancets, and lancing gun. Additionally, these steps help to synchronize purchasing of disposables which reduces frequent trips to a pharmacy. The consolidation of the testing components will also make testing faster, and less dependent on finding a suitable environment, such as a washroom, test surface, and/or disposal bin. As such, the Applicants consolidated device should be safer and more user friendly.

A third developmental goal of the consolidated testing apparatus of the present invention is the ultra-miniaturization of the sample size required to be taken from a patient in order to perform the test. Ultra-miniaturization of sample size is enabled by a proprietary thin film, capillary-augmented sample acquisition process which is described in more detail in Kloepfer et al., U.S. patent application Ser. No. 09/696,156, which was filed on 25 Oct. 2000, and contains a disclosure which is incorporated herein by reference.

SUMMARY OF THE INVENTION

In accordance with the present invention, a body fluid testing device includes a body member and a tissue penetrator carried by the body member. A test strip holder is carried by the body member, and a test strip is carried by the test strip holder. The test strip is capable of receiving a body fluid thereon and processing the body fluid into a form suitable for yielding test results relating to the content of the body fluid.

In the preferred embodiment of the present invention, the device also includes a cleansing member with a pressure inducing member. The cleansing member is carried by the body member for cleansing the tissue area to be penetrated by the tissues penetrator. The cleansing member includes an aperture, and, along with the penetrator, is disposed adjacent to the first end of the body portion. The penetrator is extendable through the aperture of the cleansing member, as the penetrator moves from its retracted position, to its axially extended position. Preferably, tissue penetrator includes an actuator for retaining the tissue penetrator in the retracted position releasing the tissue penetrator upon activation by the user, to move into the extended position. The tissue penetrator can include a depth adjustor for permitting the user to adjust the axial distance traveled by the tissue penetrator between its retracted and its extended position.

The pressure inducing member preferably comprises a cap member disposed adjacent to the first end of the body member. The cap member is hingedly coupled to the body member, and is movable between a closed position, wherein the cleansing member and the penetrator are covered by the cap member, in an open position. When the cap member is closed, it is disposed generally co-axially with the body member. The cap member includes a tissue engaging rim that defines an axially inwardly extending cavity.

One feature of the present invention is testing consolidation, i.e. unification of the various components needed to test blood into a single testing device. The Applicants believe that it is advantageous to keep the testing meter as a separate component, because to incorporate a testing meter into the remainder of the components (lancet, lancet gun, test strip and cleansing swab) would make the device too expensive to be disposable. Rather, the Applicants believe that cost-efficiencies and sanitary concerns are best addressed with a removable meter that is employed with a disposable testing device that includes the lancet, lancet gun, test strip and cleansing swab.

The Applicants believe that the consolidated testing device of the present invention will greatly reduce apprehension, inconvenience and fear and should receive a warm welcome from diabetics. A reduction in the fear factor is achieved by employing a retractable lancet, which is not seen by the user, thus lessening the "needle fear" caused by the sight of a traditional exposed lancet.

In one embodiment, the testing device has a removable and replaceable swab cap holding the cleaning fluid swab. Upon removal of the peel-off lid, the swab (cellulose or polypropylene sponge) protrudes outward because of interior pressure from material elasticity. The user cleans the intended lancing site, removes the lancet cap and lances the site by applying perpendicular pressure against the skin. He then recaps the lancet unit and turns the device 180 degrees, draws the sample into the reaction capillary, waits for removal of excess blood and monitors the result.

In another embodiment, the removable lancet cap has been replaced with a living hinge snap cap. In this embodiment the cleaning swab is enclosed within the snap cap. The exterior side of the snap cap features a dome shaped pressure cup for sample enlargement (when necessary), activated by pressing the cup against the lanced site. This pressure against the lanced site helps to enhance the flow of blood from the lanced site, thus ensuring a sufficient supply of blood to meet the quantity needs of the test strip and meter.

Another aspect of the consolidated testing device feature of the present invention is that it reduces the number of separate items that the user must handle from about six items to a single item. Current SMBG systems require at least half a dozen items to enable a user to perform a blood test. In addition to the meter, these items include a test strip, lancet, lancet shooting device, calibration strips, alcohol swab, bags, vials, and caps. These items must be removed from a common pouch, assembled and handled to perform a single, sterile test, and then repackaged. The proposed consolidated technology would require a person to handle only a single disposable, the test strip/lancet/swab/pressure cup unit (along with a meter), thereby reducing product clutter. Besides greatly facilitating ease and speed of performance, this unitization concept has the potential to streamline parts inventory control and save diabetics intermittent trips to the pharmacy every time they run out of a particular item.

The consolidation concept is particularly suited for alternate site testing (AST such as by withdrawing blood from the forearm, rather than a finger tip. AST is becoming increasingly popular because (1) pain from finger sticks is eliminated, and (2) available lancing surfaces are significantly increased. The amount of blood obtainable from a forearm stick is one magnitude less than what can be acquired from a finger stick. Because of this, many prior art blood test systems were unable to utilize AST, as insufficient amount of blood were obtained from these AST sites to satisfy the requirements of either or both of the test strip and meter.

Although Bayer and MediSense have introduced vacuum assisted devices that are useful for obtaining greater blood flow quantities from alternative sites, the Applicants have found that the application of a vacuum is unnecessary. Surprisingly, the Applicants have found that pressure applied around the lancing site will cause increased blood flows. One feature of the present invention is that a pressure inducing component such as a pressure cup is provided that increases blood flow at alternative stick sites, without the need for a vacuum assist Through repeated experiments (at two different body sites) the Applicants have demonstrated that sample volumes can be increased 5-10 times when a pressure cup is applied as opposed to unassisted blood acquisition. In these studies we used one of the smallest lancets currently marketed, the Roche Softclix, at the lowest of its 11 depth settings=0.5). With unassisted lancing, blood volumes obtained were between 0 and 200 nanoliter.

In some sticks no blood was obtained at all. However, even in most of those "no-blood-obtained" cases, sufficient blood could be extracted when a cup was pressured against the sticking site. Such a pressure cup can be incorporated into the consolidated test device.

Several advanced designs of consolidated teststrips enhancing functionality and ergonomics are part of the present invention. Advantages of the advanced designs are: (1) elimination of one part (separate swab cap), streamlining production; (2) continuously adjustable depth penetration of lancet owing to a co-molded, eccentric cam lancet cap stop wall; (3) capacity for repeat lancing in the event of an insufficient sample volume; (4) provision of a pressure cup to enlarge sample volumes obtained from sticks <300 nL; (5) the repositioned "living hinge" swab cap serves as a protective cover for the lancet, providing additional safety by preventing presence of used and exposed lancets in temporary and mass disposal, and (6) substantially improved user handling and ergonomics.

The entire consolidated test strip can be manufactured from three (3) injection molded parts joined together by two (2) snap-in connections, assembled with the punched foils that contain the test chemistry.

Additional objects, advantages and novel features of the invention are set forth in the description that follows, and will become apparent to those skilled in the art upon their viewing the drawings in connection with the following description.

DETAILED DESCRIPTION

Figure 3:
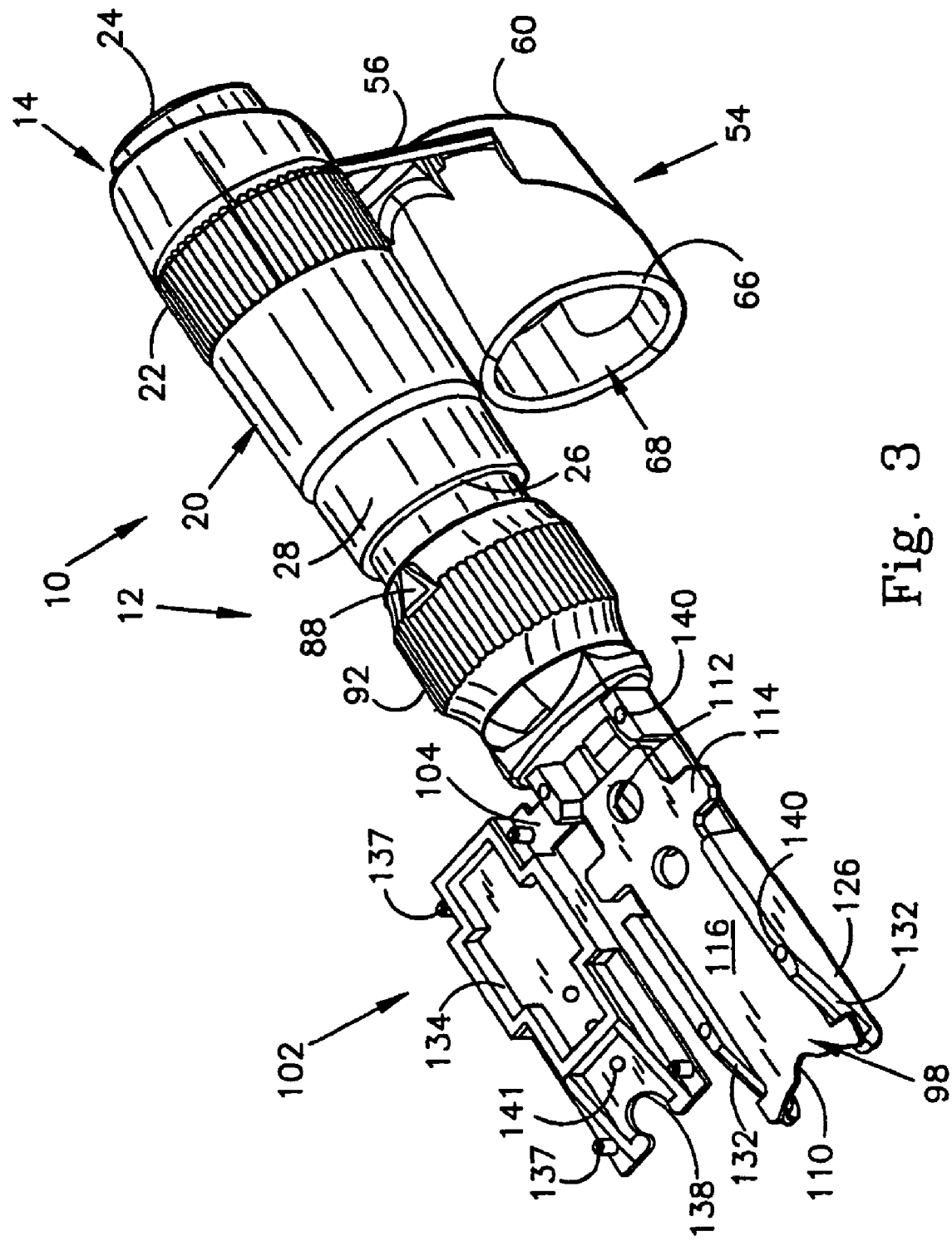
FIG. 3 is an assembled perspective view of the present invention.
Figure 4:
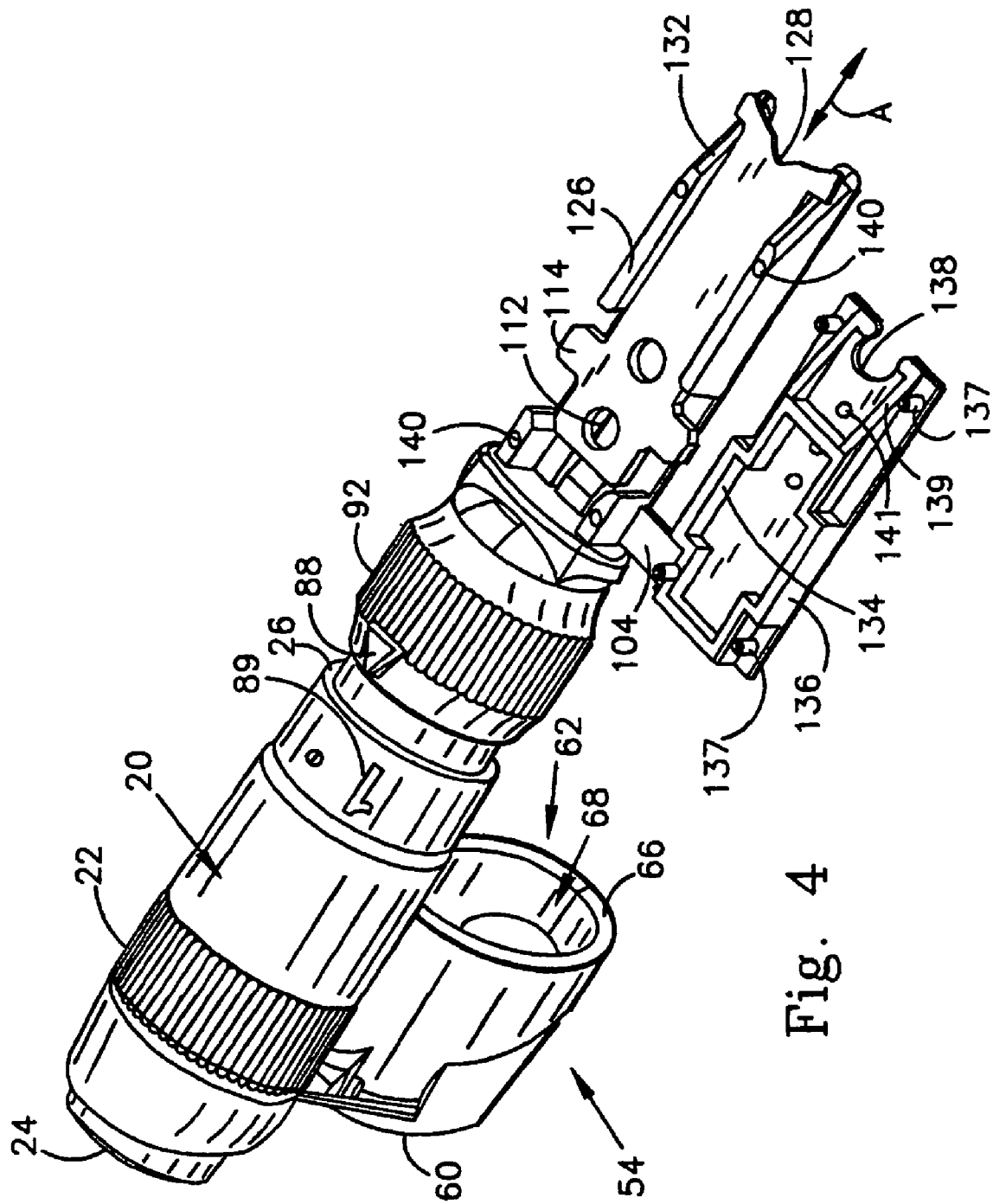
FIG. 4 is another assembled perspective view of the present invention.

The first embodiment of the testing device 10 of the present invention is shown in FIGS. 1-4 as including a body 12 that includes a first end body portion 14 that is attachable to and joinable with a second body portion 16 to form the assembled testing device 10, as shown in FIGS. 3 and 4. The testing device 10 is generally pen-shaped, and includes a longitudinally extending axis A, which will be used as a reference point to describe the various surfaces and directional extent of the components of the testing device 10. The first end body portion 14 includes a radially outwardly facing cylindrical surface 20 having a knurled or otherwise roughened gripping surface 22 for enhancing the user's ability to grip and control the device 10. The first end body portion 14 also includes an arbitrarily designated proximal end 24 and a distal end 26. A reduced diameter portion 28 is disposed adjacent the distal end 26. The reduced diameter portion 28 is sized for interiorly receiving the proximal end of the second end body portion 16 within the generally hollow interior passageway 30 of the distal end 26. The generally hollow interior passageway 30 is defined by a generally cylindrical interior surface 32.

A bundt cake pan-shaped cleansing member receiver (not shown) is disposed within the interior of the proximal end 24 of the first end body portion 14, and is sized and configured for receiving a toroidal-shaped absorbent cleansing member 36, that preferably comprises an absorbent pad that absorbantly holds a disinfecting agent, such as a relatively non-volatile alcohol, or other disinfectant, such as those containing anti-microbial and anti-germ agents such as Nonoxyl-9. The cleansing member 36 has a radially extending, axially outwardly facing surface 38, and a radially extending, axially inwardly facing surface 40.

An axially extending central aperture 42 extends through the cleansing member 26 between the inwardly and outwardly facing surfaces 38, 40, and is sized to be received by the axially extending hollow central finger (not shown) of the cleansing member receiver. As will be described in more detail below, the central aperture 42 and hollow finger of the cleansing member receiver are sized and positioned to permit lancet 50 to pass therethrough, so that when lancet 50 is in its fully extended position, the penetrating tip 81 of the lancet 50 will extend axially outwardly beyond the axially extending outwardly facing surface 38 of the cleansing member 36. Of course, when the lancet 50 is in its retracted position, the penetrating tip 81 is disposed axially inwardly of the axially outwardly facing surface 38 of the cleansing member 36, so that a person using the cleansing member 36 to disinfect and clean a body tissue area prior to penetration does not stick himself with the lancet 50.

Cap member 54 is hingedly coupled to the first end body portion 14 by a snap-type living hinge member 56. The cap member 54 is movable between an open position (as shown in the figures,) wherein the longitudinal axis of the cap member 54 is generally parallel to the longitudinal axis A of the testing device, and a closed position. In the closed position, the cap member 54 rotates 180 degrees about the pivot formed by hinge member 56, and is disposed in a generally co-axial relationship with the proximal end of the first end body portion 14. When in a closed position, end 60 of the cap member 54, that is shown as being a proximal end in FIG. 1, becomes the distal end 60 of the cap member 54, and the other end 62 of the cap member 54, that is shown in FIG. 1 (in the open position) as being the distal end, becomes the proximal end 52 of the cap member 54.

The distal end 60 of cap 54 is designed to mate with the proximal end 24 of the first body portion 14, when the snap-type living hinge 56 moves the cap member 54 to its closed position. Although, ideally the mating between the distal end 60 of the cap member 54 and the proximal end 24 is a sealing relationship of the type that prevents any disinfecting agent within the cleansing member 36 from evaporating, it is possible that some sort of covering will need to be placed over the axially outwardly facing surface 38 of the cleansing member 36 to prevent any volatile disinfectant absorbed within the cleansing member 36 from evaporating during the time period between when the device 10 is manufactured and when the device 10 is finally used by a patient.

Figure 1:
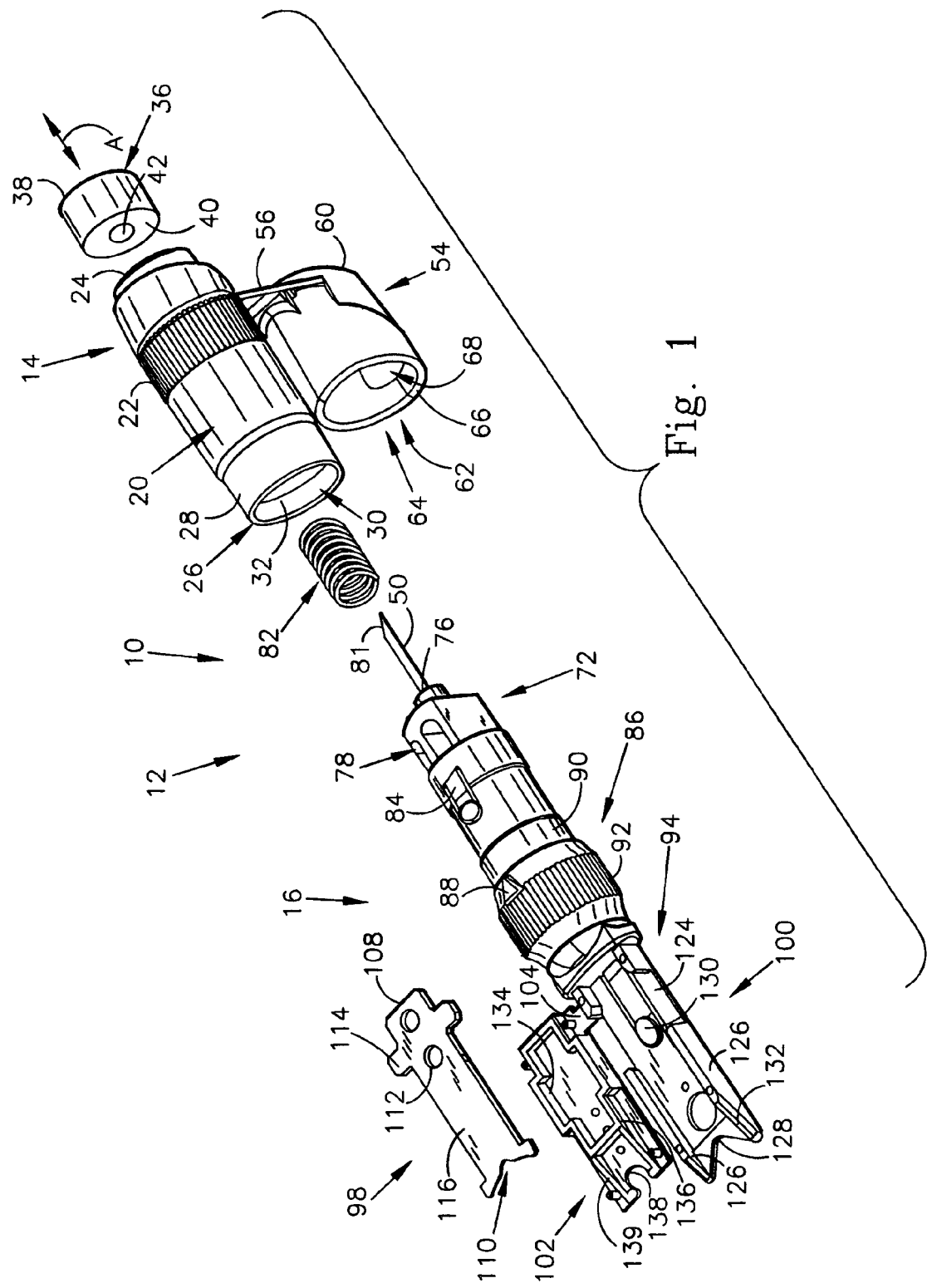
FIG. 1 is an exploded perspective view of the consolidated blood testing device of the present invention.
Figure 2:
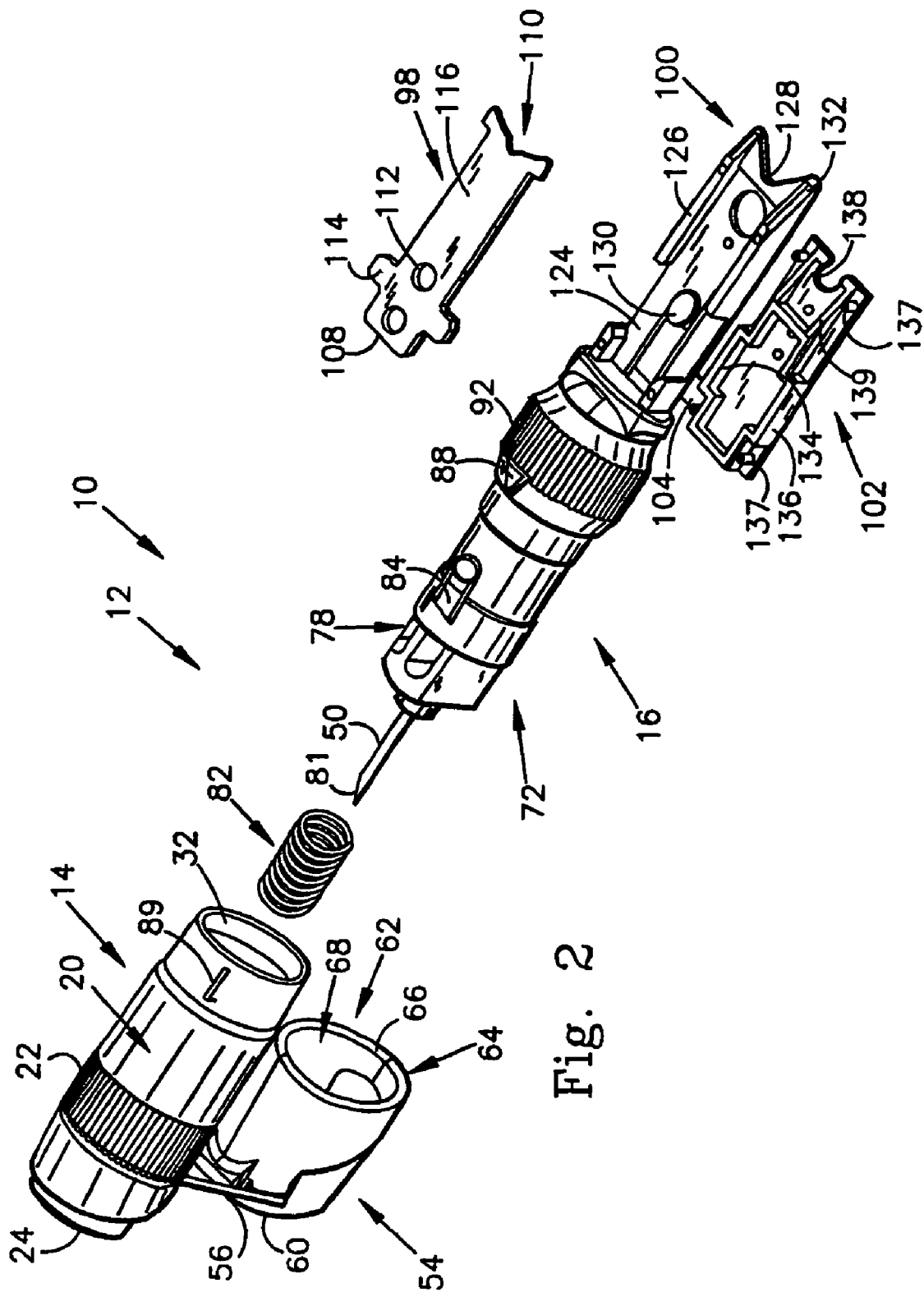
FIG. 2 is another exploded perspective view.

As stated above, the living hinge members 56 are "snap-type" living hinge members that are designed to be spring-tensioned so that the cap 54 only finds a rest position when the cap 54 is either in its open position as shown in FIG. 1, or in its closed position wherein the cap 54 is disposed co-axially with the second body portion 14. This snap-type spring arrangement of the living hinge 56 facilitates manipulation of the device by the user, because the opening of the cap 54 will cause it to snap into its fully open position, rather than to flop around within an arc of open positions.

The proximal end 62 of the cap member includes a pressure cup 64 that is defined by a circumferential pressure inducing lip 66, and a cup-shaped interior 68. As will be described in more detail below, placement of the circumferential pressure exerting lip 66 on a tissue area that surrounds a tissue site that has been penetrated by the tissue penetrator, along with the application of a moderate amount of axially directed force, has been surprisingly found by the Applicants to induce a flow of blood out of the penetrated site to enhance the volume of blood that is obtained from the penetrated site. This feature has the advantage of enabling the testing device to obtain a sufficient quantity of blood from testing sites, such as the forearm, that formerly were unuseable by blood test strips because they normally did not bleed sufficiently to yield enough blood to enable the user to perform a blood test. In the prior art, this inability to obtain a sufficient quantity of blood required the user to obtain blood samples from sticks made on the user's fingertips, as the finger tips yielded sufficient blood.

An axially movable tissue penetrator 72, that is movable between the retracted position, and an extended position includes a needle-like tissue penetrating lancet 50, that is fixedly coupled to an axially movable mounting carriage 78. It will be noted that the mounting carriage 78 and the lancet 50 are coupled to the first end of a portion 16. However, when the device 10 is assembled, as shown in FIGS. 3 and 4, the carriage 78 and lancet 50 are interiorly received within the hollow interior 30 of the first end portion 14, so that the penetrating tip 81 of the lancet 50 is disposed adjacent to the proximal end 24 of the first end body portion 14.

As alluded to above, the lancet 50 normally resides in its retracted position where the penetrating tip 81 is disposed axially inwardly of the axially outer facing surface 38 of the cleansing member 36, so that when the user employs the cleansing member 36 to cleans his finger, he does not stick himself with the tip 81 of the lancet 50. The lancet 50 is also movable into an extended position, wherein it is moved axially outwardly, under the force of a biasing member, such as spring 82 so that the penetrating tip 81 extends axially outwardly beyond the axially outer facing surface 38 of the cleansing member 36, to prick the tissue site to cause bleeding therefrom.

One end 76 of the lancet 50 is coupled to a mounting collar on the carriage 78, that couples the lancet 50 to the carriage 78. Lancet 50 can be fixedly coupled to the movable carriage 78, and the carriage 78 can be designed to move axially, to cause the axial movement of the lancet 50. Alternatively, the carriage 78 can be fixedly positioned, and the lancet 50 be designed to be axially moveable relative to the carriage 78.

Spring 82 is provided for biasing the lancet 50 to move in an axially outward direction, to engage tissue. A trigger member 84 is provided for maintaining the lancet 50 in its retracted position, until the user actuates the trigger 84, that permits the spring 82 to move the lancet 50 to move axially outwardly, to thereby prick a tissue surface. Although a single spring 82 is shown in the figures for biasing the lancet 50 to move axially outwardly, a dual-acting spring arrangement can be designed that enables the lancet 50, upon actuation of trigger 84 to move axially outwardly to engage a tissue surface, with a second spring being provided to move the lancet 50 axially inwardly to retract it after the tissue poke is made.

A depth gauge 86, including a camming surface for facilitating axial movement (not shown) is provided for enabling the user to adjust the extent of axial movement of the lancet 50, that permits the user to adjust the depth to which the penetrating tip 81 of the lancet 50 penetrates the tissue surface of the user. As will be appreciated, some users would prefer that the lancet 50 penetrate more deeply, to ensure a better blood flow and supply, whereas others would prefer that the lancet 50 make a more shallow penetration of the tissue, that would likely be less painful. The depth gauge 86 includes pointer 88 that is reconcilable with a gauging surface (surface 28) for maintaining one or more numerical indicators, such as numerical indicator 89 (FIG. 4) that provides an indication to the user of the relative depth to which the lancet 50 will penetrate. A gripping surface 92 is provided for permitting the user to rotate the cylindrical gauging wheel that contains gripping surface 92 on pointer 88 (or alternately, to rotate first end body portion 14) to permit the user to vary the insertion depth of the lancet 50.

The second end body portion 16 also includes a test strip component 94 that is disposed generally at the distal end 96 of the second end body portion.

Figure 8:
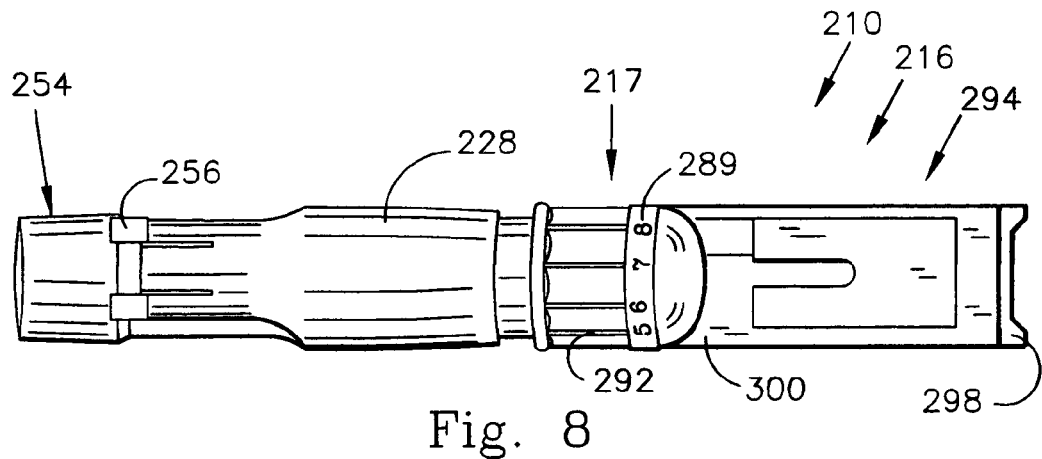
FIG. 8 is a bottom view of the first alternate embodiment of the present invention.
Figure 9:
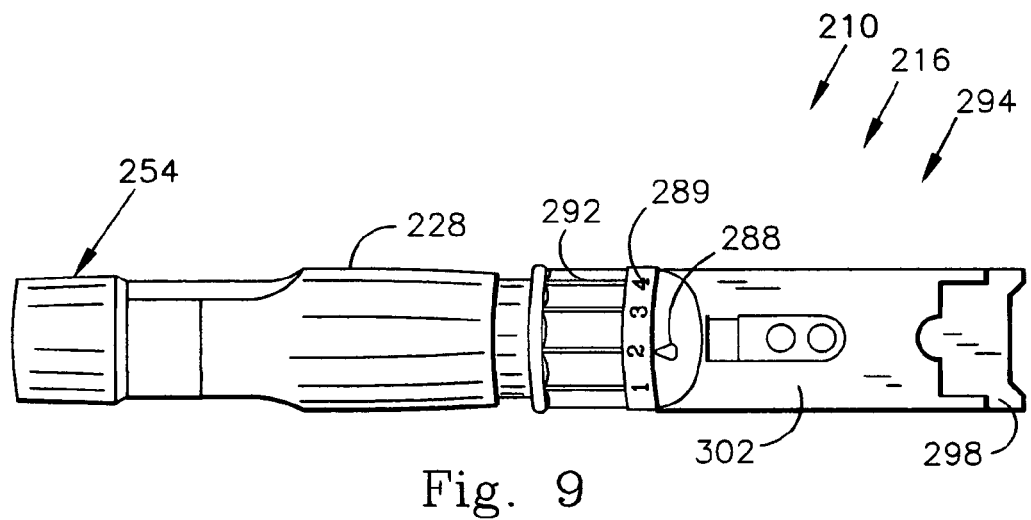
FIG. 9 is a top view of the first alternate embodiment of the present invention.
Figure 10:
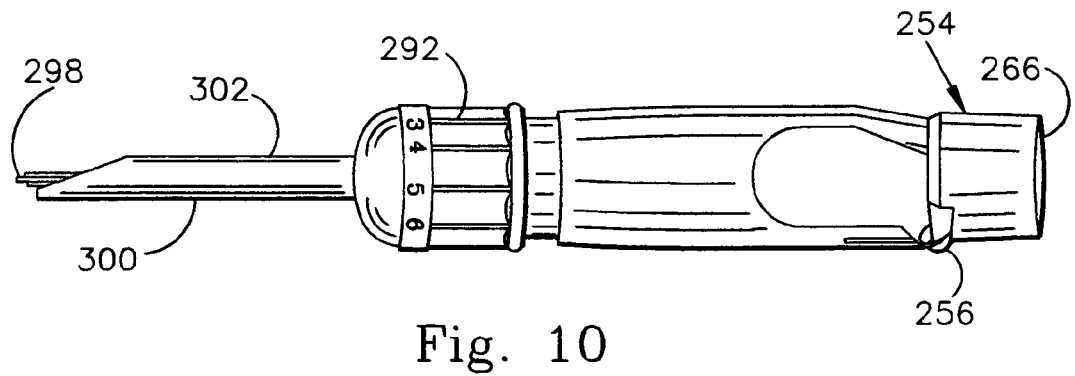
FIG. 10 is a side view of the first alternate embodiment of the present invention.
Figure 11:
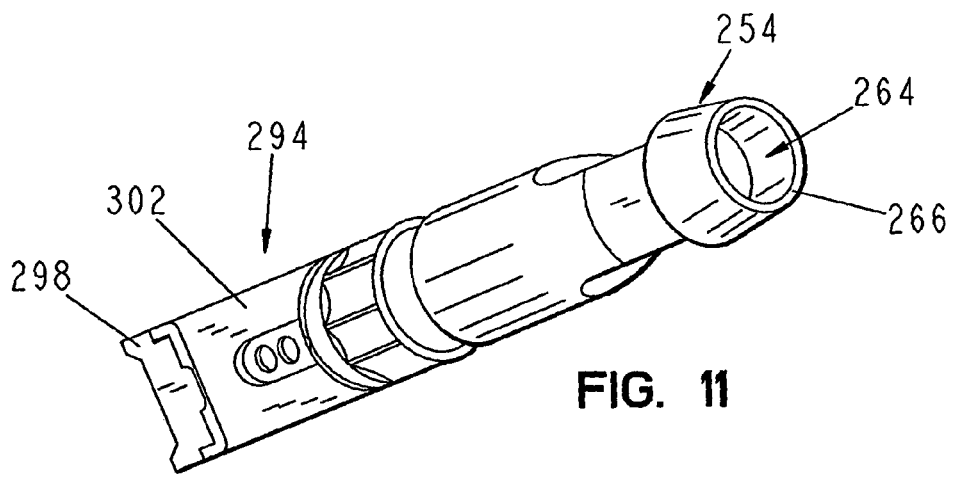
FIG. 11 is a perspective view, illustrating the pressure cap of the present invention.
Figure 12:
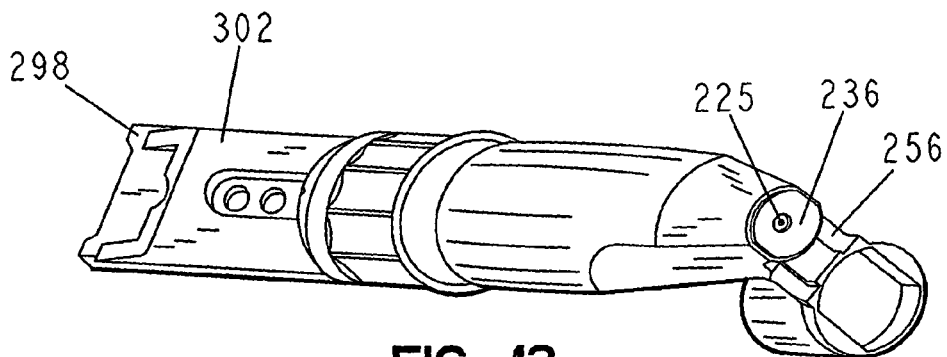
FIG. 12 is a perspective view, wherein the pressure cap in its open position, and the cleansing swab is exposed.
Figure 13:
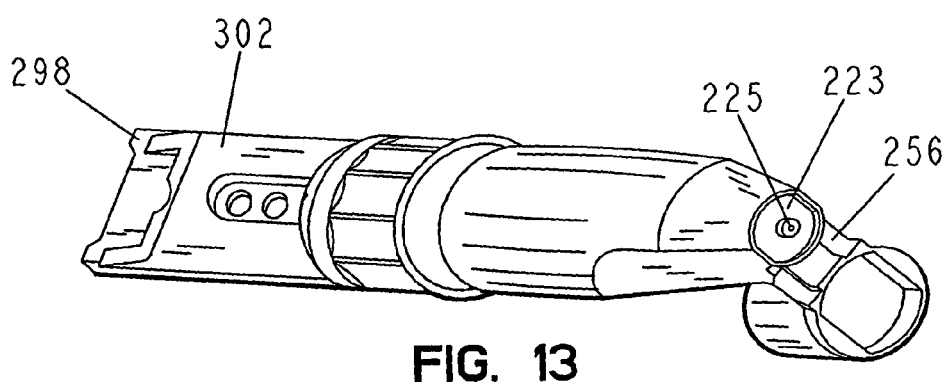
FIG. 13 is a perspective view, similar to FIG. 12, but with the cleansing swab removed to illustrate the cleansing swab receiving chamber.

The test strip component 94 is disposed at the distal end of the second end body portion 16, and includes four primary components, a test strip 98, a test strip holder 100, a test strip retainer 102, and a living hinge mechanism 104 for hingedly coupling the test strip holder 100 to the retainer 102. Test strip retainer 102 is movable between an open position (as shown in the figures) and a closed position (see, e.g., FIGS. 8-10). When the test strip retainer 102 is in its closed position, the test strip 98 is sandwiched between the test strip retainer 102 and the test strip holder 100 to maintain the test strip 98 in its appropriate position on the device 10.

The test strip 98 is preferably a capillary containing test strip of the type described in Kloepfer, Kloepfer and Roach patent application Ser. No. 09/696,156, that is also assigned to the Assignee of the instant invention. Although the disclosure relating to the test strip of the '156 application is incorporated herein by reference, and need not be repeated further here, the test strip 98 is designed to separate the colored (primarily hemoglobin) components of the blood from the clear, primarily plain components of the blood, to provide a generally clear analyte fluid, that can then be reacted with reagents contained on the test strip to form either a calorimetric or non-colorimetric reaction product that can then be analyzed either visually, or through the use of a meter (not shown).

The test strip 98 includes a collection component that comprises an inlet, a collection capillary structure to draw the fluid of interest into the collection component via the inlet exerting capillary forces upon the fluid applied to the inlet. The device also includes a film that is operable to collect the correct analyte from the fluid as the fluid is drawn over the film. A wicking component is provided that is coupled to the collection component, and is structured to draw the fluid over the film and into the wicking component. The wicking component exerts sufficient capillary force on the analyte fluid to effectively sweep the film free of particulate matter (e.g. hemoglobin) of the fluid, without filtration or other mechanical removal devices. The functional components described above of the test strip are incorporated into test strip 98.

The shape of test strip 98 is dictated largely by its need to incorporate the above-discussed functional components, while fitting into the test strip holder 100 and test strip retainer 102, while still being insertable into an appropriate glucose meter so that the glucose meter can "read" the reaction product analyte that is drawn from the body fluid (e.g. blood) that is placed on the collection component of the test strip 98. The test strip 98 includes a proximal end 108 and a fluid sample receiving distal end 110. Generally, blood placed on a test strip flows from the distal end 110 toward the proximal end 108.

Test strip 98 includes finger receiving apertures 112 that are designed for receiving an upstanding finger 130, whose purpose is to fixedly position the test strip 98 on the test strip holder 100 and receiver 102. A pair of radially extending tabs 114 are formed on the test strip 98 to also help to fixedly position the test strip 98 on the test strip holder 100 and receiver 102.

The test strip 98 includes a body fluid receiving upper surface 116 having a separating portion and a capillary containing portion, a wicking component portion, and a reagent impregnated portion, as taught by the above Kloepfer, Kloepfer and Roach patents. Generally, only one side of the test strip 108 needs to be treated with the functional components, as blood is generally only placed one side 116 of the test strip 98.

The test strip holder 100 includes a generally planar base for receiving test strip 98 and a set of upstanding perimetral side walls 124 for capturing the test strip 98, and maintaining it on the holder 100 in a snug relationship. The test strip holder 100 also includes a concave distal surface 128 that facilitates the introduction of blood to the test strip 98, and a strip retaining upstanding finger 130, that may be movable between a strip 98 engaging position and strip 98 releasing position. A pair of ramping surfaces 142 are formed on the frontal distal surface of the upstanding side walls 126 to facilitate the lifting of the test strip 98 by an appropriately designed glucose meter (not shown).

The test strip retainer 102 is designed to matingly engage with the test strip holder 100, for retaining the test strip 98 by securing the test strip 98 on the test strip component 94 of the blood testing device 10. The test strip retainer 102 is movable between an open position, such as shown in FIGS. 1-4, and that permits the test strip 98 to be inserted onto and/or removed from its engagement with the test strip holder 100; and a closed position (see, e.g. FIG. 8) wherein the test strip retainer 102 frictionally engages the test strip holder 100, so that the test strip retainer 102 is positionaly secured onto the test strip holder 100, to positionaly secure and retain the test strip 98 onto the test strip component 94. When so engaged, the test strip 98 is sandwiched between the planar base 124 of the test strip holder 100, and test strip retainer 102.

The test strip retainer 102 includes upstanding walls 136 for engaging the upper surface 116 of the test strip 98. The test strip retainer 102 is hingedly coupled to the test strip holder 100 by a living hinge 104, and includes a generally perimetral strip engaging retaining wall set 134 that is designed to be disposed above the upper surface 116 of the test strip 98.

The distal portion of the test strip retainer 102 includes a concave cut-out portion 138 for facilitating the introduction of blood onto the test strip of the upper surface 116 of the test strip 98. A pair of complimentary ramping surfaces 139 are formed on the distal end of the retainer 102, and are provided for facilitating engagement of the testing strip component 94 with an appropriate glucose meter. The primary purpose of the ramping strip surfaces 132, 139 is to permit a mechanism (not shown) within the glucose meter to lift the strip 98 as it is inserted into the meter for better fitting of the strip by the meter.

Another feature of the strip is the sufficient sample indication window 141. This allows the meter to interrogate the strip in the reservoir to insure sufficient sample has been applied prior to giving a test result.

As is best shown in FIG. 3, the retainer 102 includes four upstanding studs 137 that are sized and positioned for being received into four complimentary apertures 140 that are formed on the test strip holder 100. When the studs 137 are inserted into the apertures 140, the studs 137 fixedly engage the apertures 140 to maintain the retainer 102 in a secure frictional engagement with the holder 100.

Figure 7A:
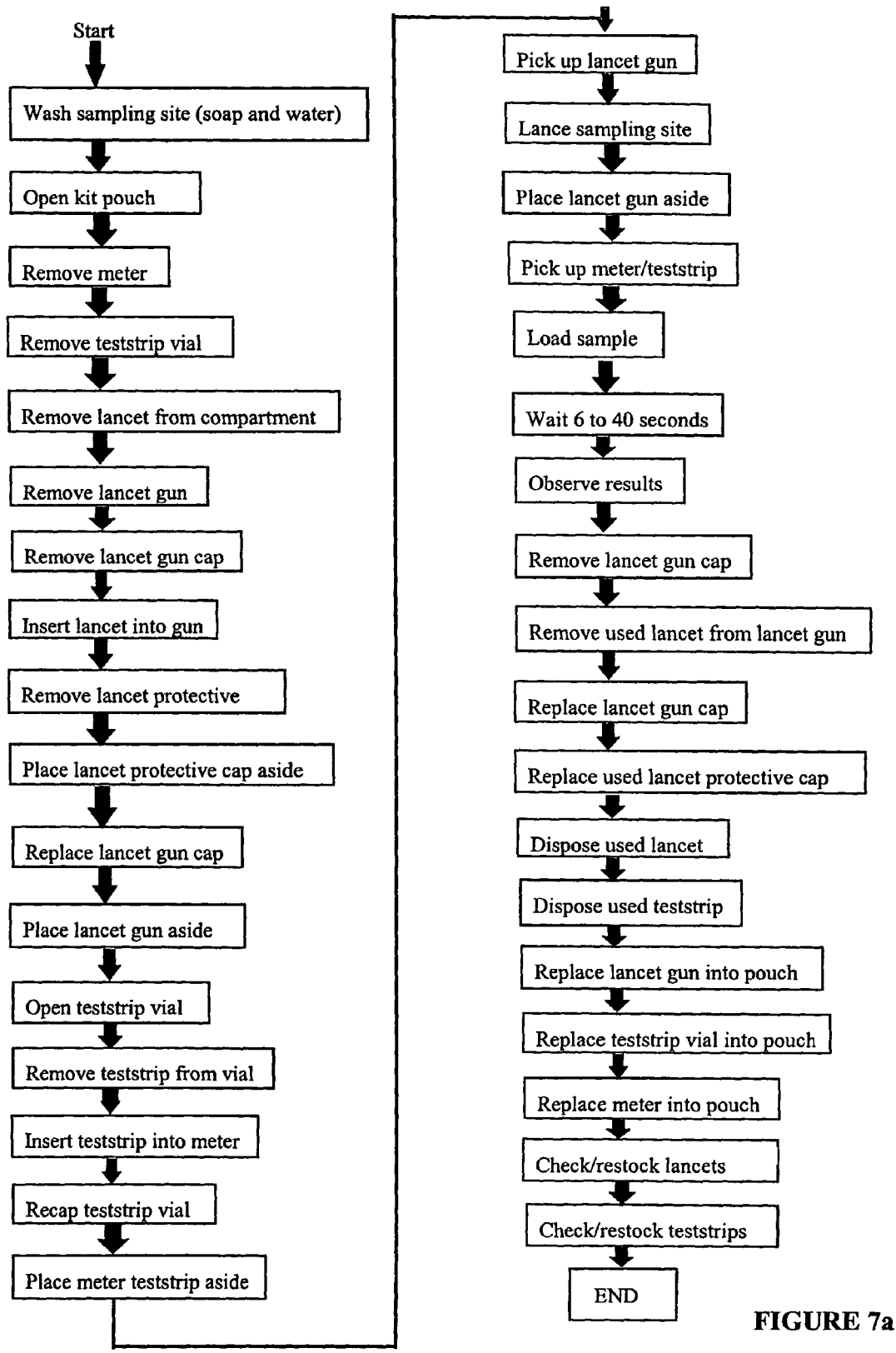
FIG. 7a is a schematic flowchart illustrating the steps necessary to perform a blood test using the prior art.
Figure 7B:
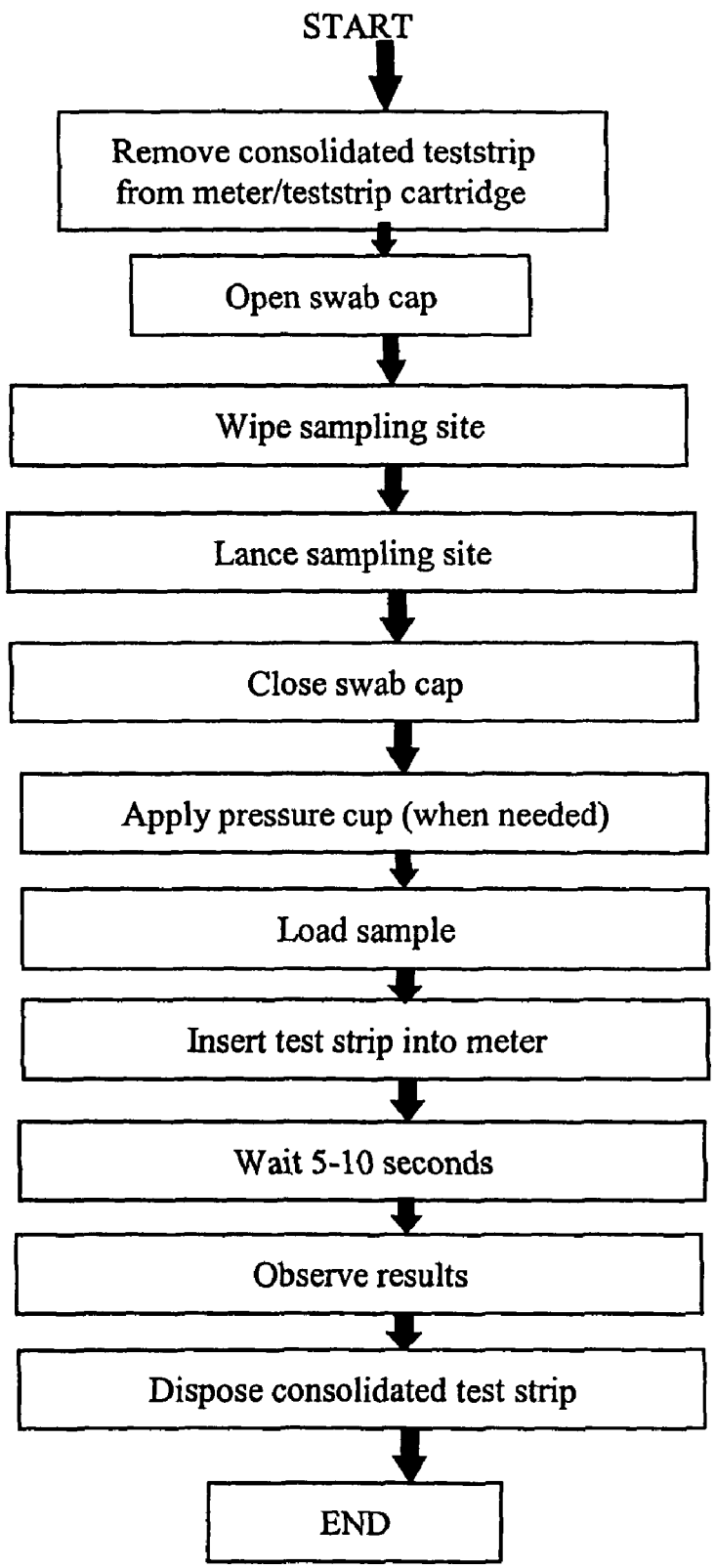
FIG. 7b is a flowchart illustrating the steps necessary to perform a blood test using the testing device of the present invention.

Your attention is now directed to FIG. 7b, that comprises a flow chart describing the manner in which the test strip device 10 is used.

First, the test strip device 10 is removed from its packaging. When packaged, the cap 54 is placed in its co-axial relationship with the second end 14 of the testing device 10, so as to create a seal against the cleansing member 36, that helps to prevent the cleansing member 36 from drying out.

Figure 14:
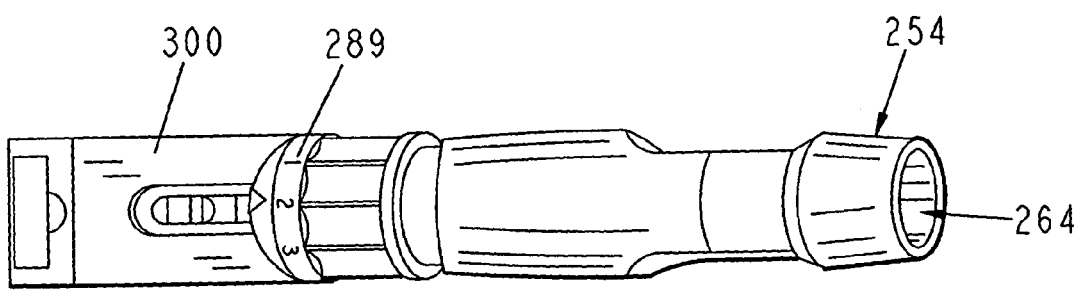
FIG. 14 is a top view thereof showing the chemistry strip removed.
Figure 15:
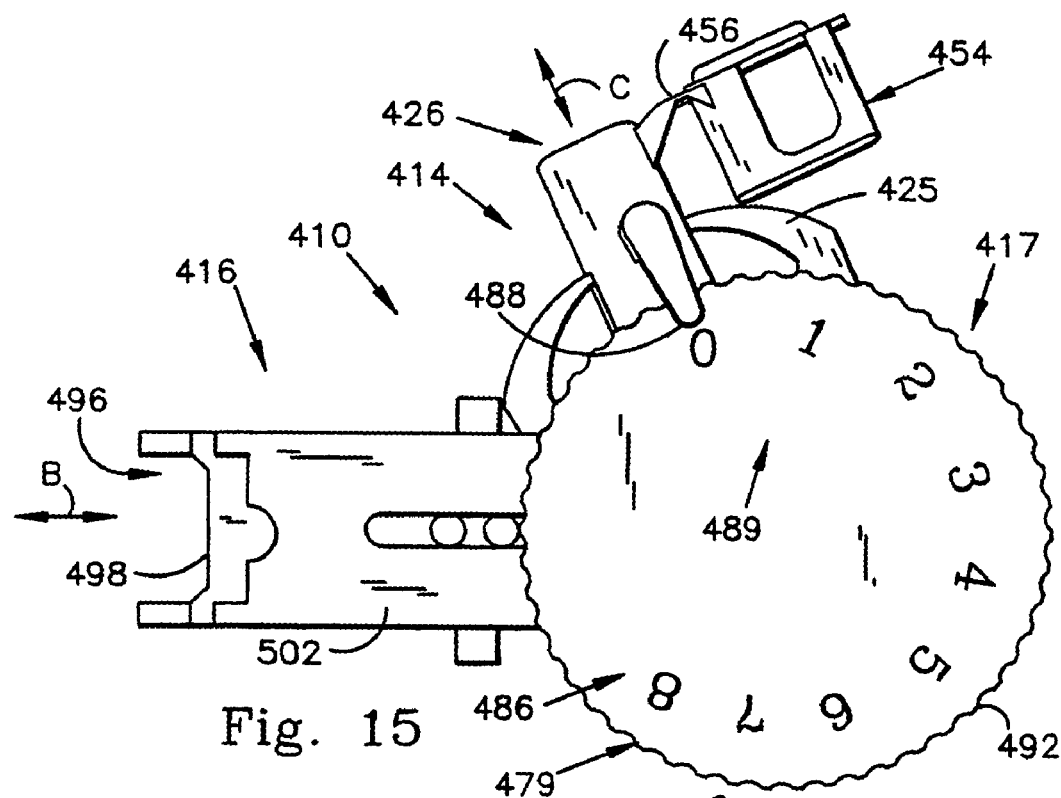
FIG. 15 is a bottom perspective view of a second alternate embodiment of the present invention.
Figure 16:
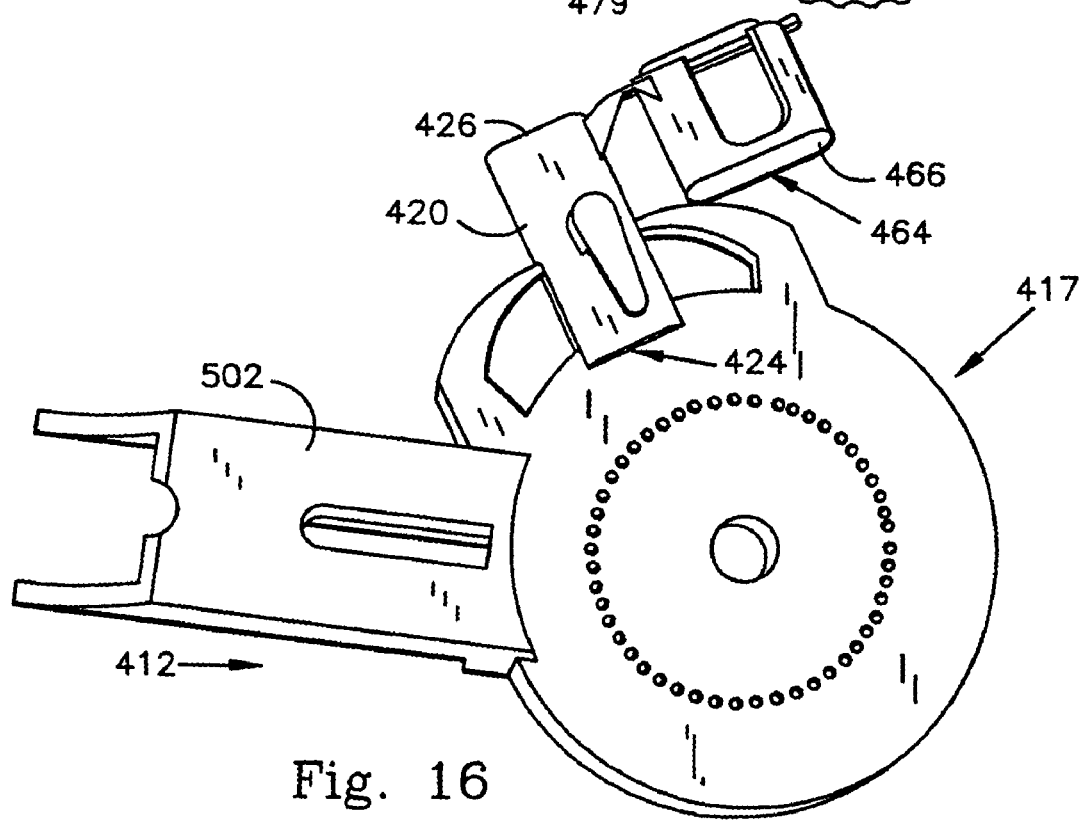
FIG. 16 is a top perspective view of the perspective view of the second alternate embodiment of the present invention, with the dial cap removed.
Figure 17:
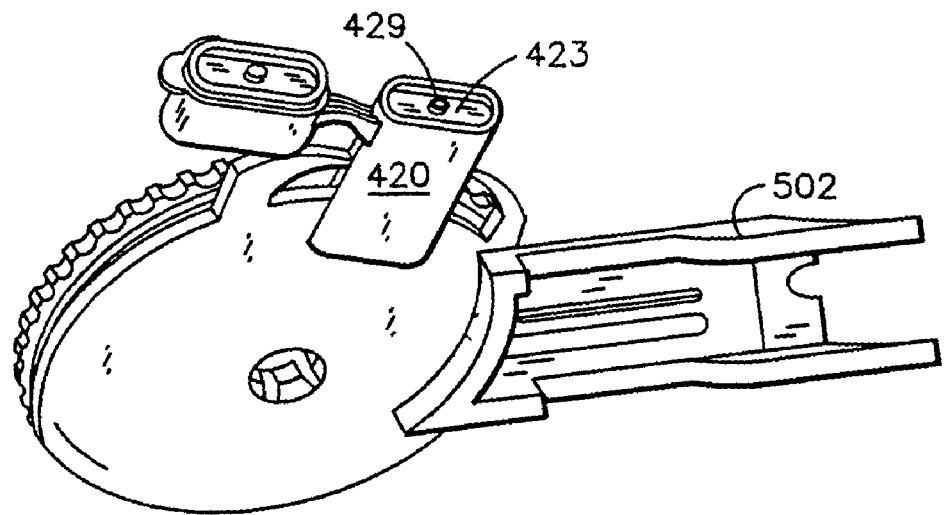
FIG. 17 is a bottom perspective view thereof.
Figure 18:
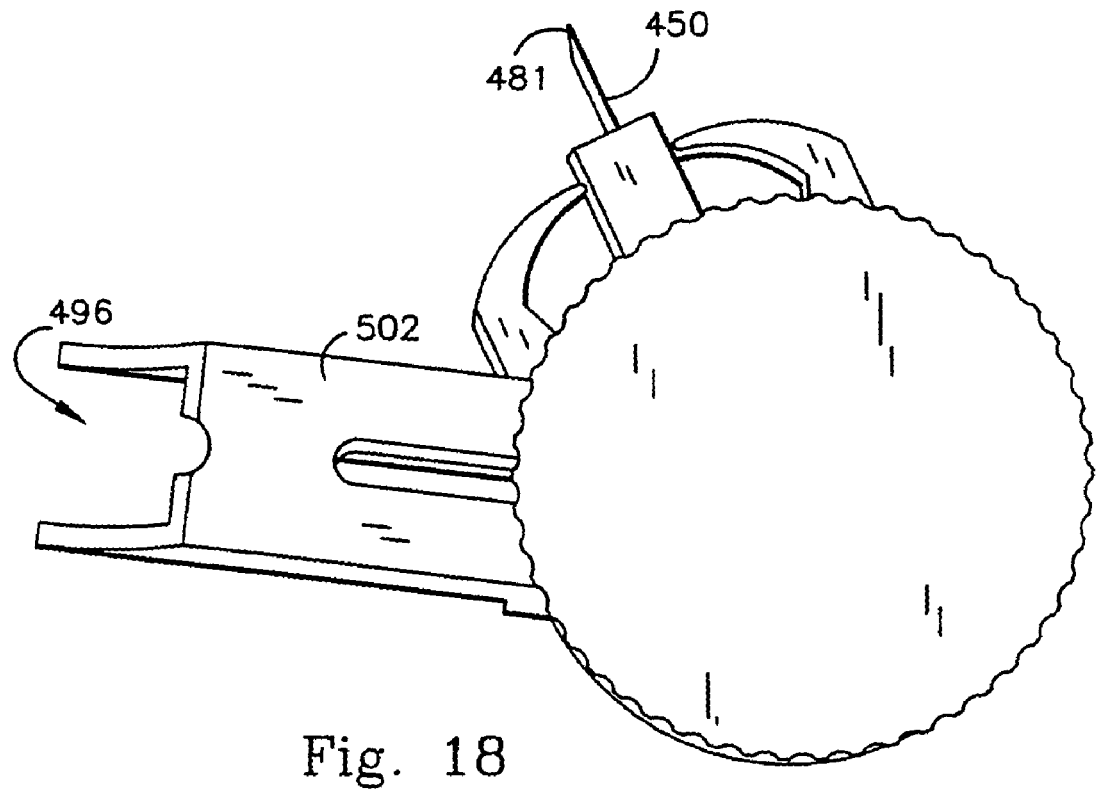
FIG. 18 is a top view of the present invention, similar to FIG. 17 however with the dial member included and the lancet cap removed.
Figure 19:
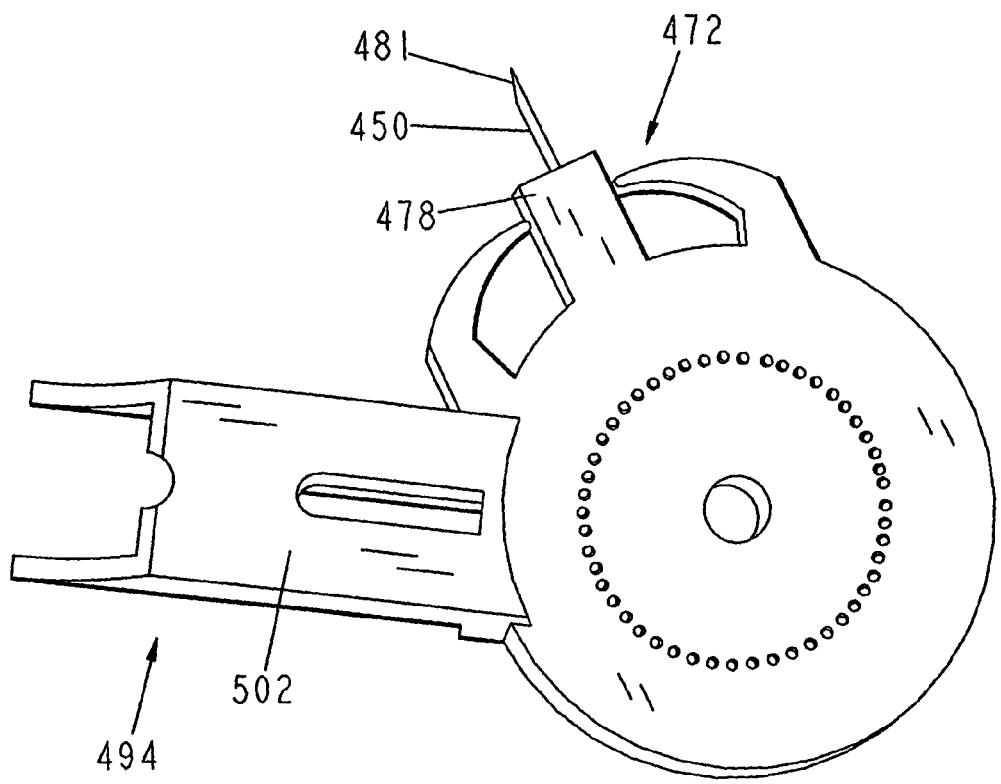
FIG. 19 is a top perspective view of the base member, including lancet of the second alternate embodiment.
Figure 20:
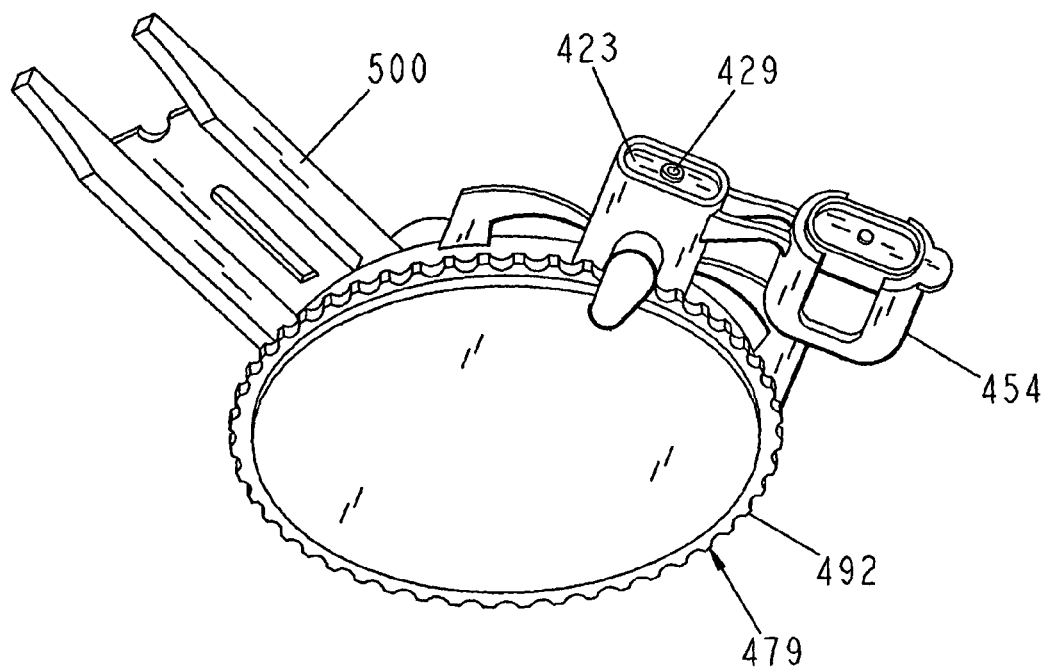
FIG. 20 is a perspective view, second alternate embodiment with the dial cap in place and the cleansing swab removed.

When the device 10 is removed from its packaging, the cap 54 is opened, and moved from its co-axial position (see, e.g. FIG. 14) to its parallel axis position, as shown in FIGS. 1-4. The user then employs the cleansing pad 36 to wipe the cleansing pad on an area of body tissue that the user desires to have penetrated by the lancet 50 in order to remove a blood sample. After the area around the testing site is wiped with the cleansing pad 36, the testing site is lanced with the user actuating trigger mechanism 94, to permit the spring 82 to move the lancet 50 axially, so that the penetrating tip 81 of the lancet 50 penetrates the skin, to thereby allow blood to flow from the puncture site. The depth to which the lancet 50 will insert itself into the skin is governed by the setting established by the user through the use of the depth gauge 86.

After the site is lanced, cap 54 is then moved back into its co-axial position, primarily to help reduce the likelihood that the user will re-stick himself with the lancet 50. As described above, the lancet 50 can be designed with a two-way biasing mechanism so that the lancet 50, after it is moved axially to engage the skin, will fall into the influence of a counter-spring to withdraw the lancet back below the axially outwardly facing surface 38 of the cleansing member 36, to reduce the likelihood of such unintentional "sticks".

From a functional perspective, an important reason to close the swab cap 54 is that it enables the user to employ the pressure cup 64 to enhance the flow of blood from the penetrated test site. Although it is likely that the pressure cup 64 would not be needed in all circumstances, such as those circumstances where the site that is lanced is a fingertip, the pressure cup 64 is especially useful when the lanced site is a relatively slower bleeding site such as a forearm.

The circumferential lid 66 of the pressure cup 64 is then placed around the lanced site, and axially directed pressure is exerted against the body tissue. This causes additional quantities of blood to flow out of the lanced site. This finding was most surprising to Applicants, as enhanced blood flow was achieved by the Applicants, without the need to resort to vacuum-assisted removal as in some prior art.

When sufficient blood has been bled out of the user, the blood sample is then loaded on to the distal end 110 of the test strip 98. After a short interval necessary for the blood on the test strip to complete its journey through the capillary and wicking components of the test strip 98, the distal end of the test strip component 94 is inserted into an appropriately sized and configured glucose meter. Typically, it requires the glucose meter approximately 5 to 10 seconds in order to perform its necessary analysis of the analyte fluid contained on upper surface 116 of the test strip 98. After the glucose meter has performed its test, the user can then observe the results of the test or the display of the glucose meter, which is typically either a liquid crystal display, or light emitting diode display. After the results are observed, the testing device 10 is removed from the glucose meter, and disposed of appropriately. A visual back-up system can be used prior to disposing of the strip if the user has any doubts about the accuracy of the result (i.e. user feels bad but the result is in the acceptable range).

It is believed by the Applicants that the entire testing procedure utilizing the strip of the present invention should require only about 25 seconds of the user's time. The reader is invited to compare the number of steps using the test device of the present invention with the significantly greater number of steps required for conventional testing, which is set forth in FIG. 7*a*. It is believed by the Applicants that the consolidation of the various components upon a single testing device 10 that is accomplished with the present invention saves the user considerable amounts of time, due largely to significantly fewer number of steps required to perform testing, and the significantly fewer number of components that must be manipulated by the user. By comparison, the Applicants believe that a person using the prior art testing devices will require somewhere between 2 and 3 minutes to completely perform the task, which compares rather unfavorably to the estimated 25 seconds required by the device of the present invention.

The first alternate embodiment of the testing device 210 of the present invention is generally similar to testing device 10 in the manner it functions, but slightly different in its construction, and is shown in FIGS. 5-14 as including a body 212 that includes a first end body portion 214 that is attachable to and joinable with a second end body portion 216 via a central portion 217 to form the assembled testing device 210, as shown in FIGS. 8-14. The testing device 210 is also generally pen-shaped, and includes a longitudinally extending axis A. The first end body portion 214 includes a radially outwardly facing cylindrical surface 220 having a knurled or otherwise roughened gripping surface 222 for enhancing the user's ability to grip and control the device 210. The first end body portion 214 also includes a proximal end 224 and a distal end 226. A reduced diameter portion 228 is disposed adjacent the distal end 226. The reduced diameter portion 228 is sized for interiorly receiving the proximal end of the central body portion 217 within the generally hollow interior passageway of the distal end. The generally hollow interior passageway is defined by a generally cylindrical interior surface 232.

A bundt cake-shaped cleansing member receiver 223 (FIG. 13) having a hollow central finger 225 is disposed within the interior of the proximal end 224 of the first end body portion 214, and is sized and configured for receiving a toroidal-shaped absorbent cleansing member 236, that is identical to cleansing pad 36. As will be described in more detail below, the central aperture and hollow finger of the cleansing member receiver are sized and positioned to permit lancet 250 (FIG. 6) to pass therethrough, so that when lancet 250 is in its fully extended position, the penetrating tip 281 of the lancet 250 will extend axially outwardly beyond the axially extending outwardly facing surface of the cleansing member. Of course, when the lancet 250 is in its retracted position, the penetrating tip is disposed axially inwardly of the axially outwardly facing surface of the cleansing member 236, so that a person using the cleansing member 236 to disinfect and clean a body tissue area prior to penetration does not stick himself with the lancet 250 while wiping down the tissue area.

Cap member 254 is identical to cap 54 and hingedly coupled to the second end body portion 214 by a snap-type living hinge member. The cap member 254 is movable between an open position (as shown in the figures,) wherein the longitudinal axis of the cap member 254 is generally parallel to the longitudinal axis A of the testing device, in a closed position as shown in FIGS. 8-14.

The distal end of the cap 254 is designed to mate with the proximal end of the first body portion 214, when the snap-type living hinge moves the cap member 254 to its closed position.

Figure 5:
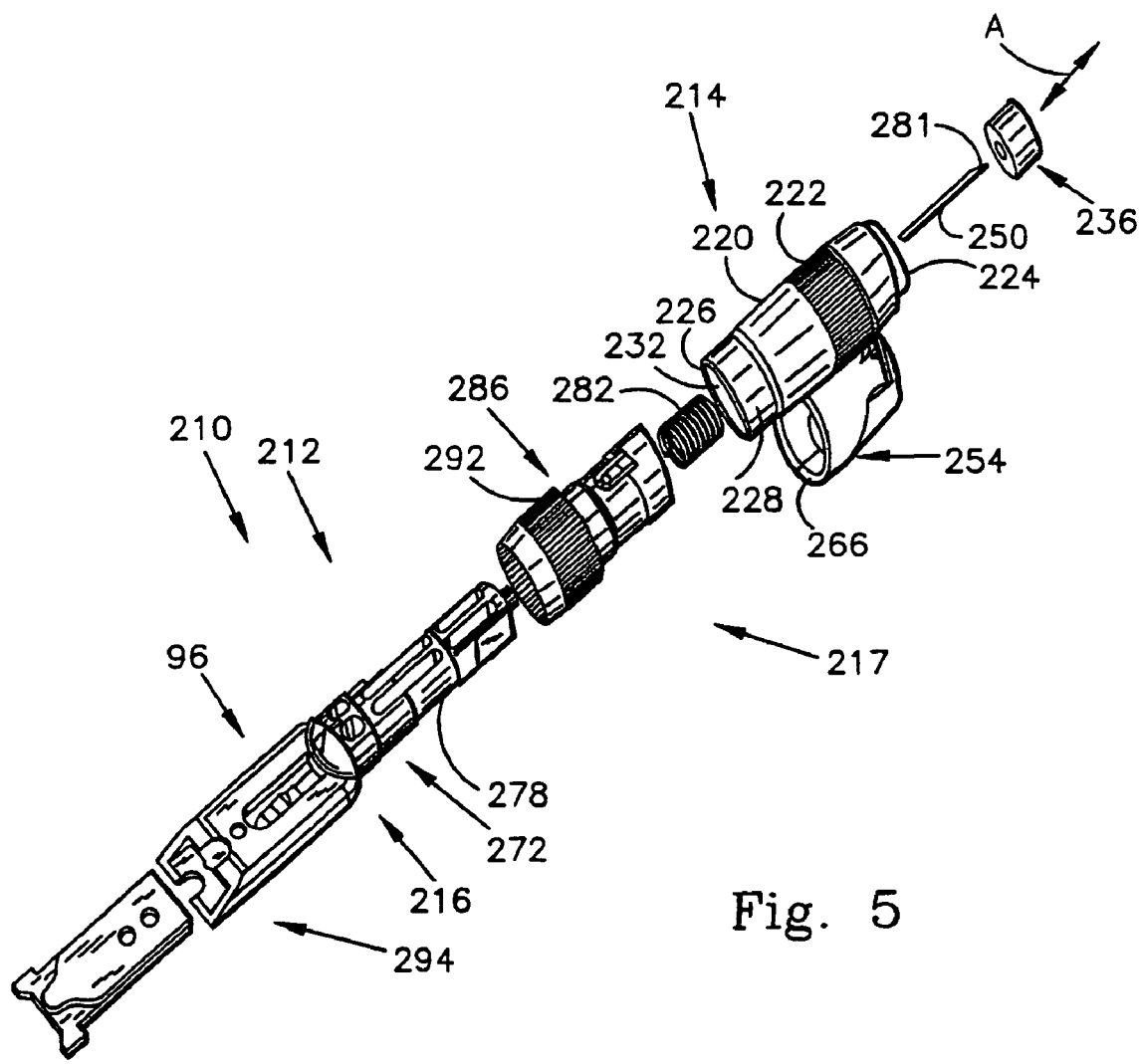
FIG. 5 is an exploded perspective view of a first alternate embodiment of the present invention.
Figure 6:
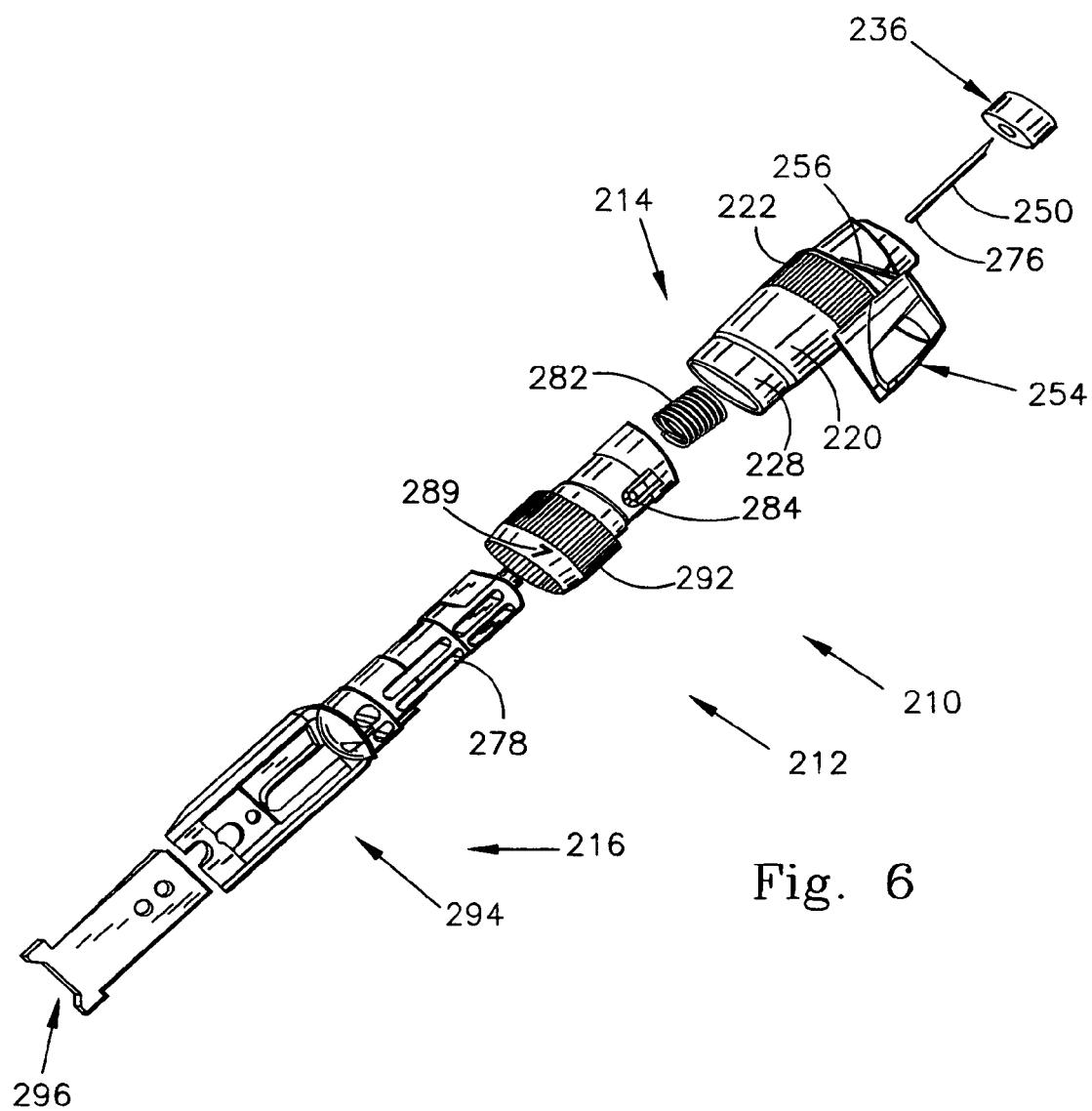
FIG. 6 is another perspective view of the first alternate embodiment of the present invention.

The living hinge members 256 are "snap-type" living hinge members that are designed to be spring-tensioned so that the cap 254 only finds a rest position when the cap 254 is in its open position as shown in FIG. 5, or in its closed position wherein the cap is disposed co-axially with the second body portion 214, as shown in FIGS. 8-14.

The proximal end of the cap member includes a pressure cup 264 that is defined by a circumferential pressure inducing lip 266, and a cup-shaped interior. As with device 10, the placement of the circumferential pressure extending lip 266 on a tissue area that surrounds a tissue site that has been penetrated by the tissue penetrator, along with the application of the moderate amount of axially directed force, has been surprisingly found by the Applicants to induce a flow of blood out of the penetrated site to enhance the volume of blood that is obtained from the penetrated site.

An axially movable tissue penetrator 272, that is movable between the retracted position, and an extended position includes a needle-like tissue penetrating lancet 250, that is fixedly coupled to an axially movable mounting carriage 278. It will be noted that the mounting carriage 278 and the lancet 250 are coupled to the first end of a portion 216, but is separated from the central portion 217 unlike testing device 10. Nonetheless, when the device 210 is assembled, as shown in FIGS. 8-14, the carriage 278 and lancet 250 are interiorly received within the hollow interior of the first end portion 214, so that the penetrating tip 281 of the lancet 250 is disposed adjacent to the proximal end 224 of the first end body portion 214. The lancet 250 is movable between a retracted position wherein the penetrating tip 281 is disposed axially inwardly of the axially outer facing surface of the cleansing member 236, so that when the user uses the cleansing member 236 to cleans his finger, he does not stick himself with the tip 281 of the lancet 250. The lancet 250 is also movable into an extended position, wherein it is moved axially outwardly, under the force of a biasing member, such as spring 282 so that the penetrating tip 281 extends axially outwardly beyond the axially outer facing surface of the cleansing member 236, to prick tissue site to cause bleeding therefrom.

One end 276 of the lancet 250 is coupled to a mounting collar on the carriage 278, that couples the lancet 250 to the carriage 278.

Lancet 250 can be fixedly coupled to the movable carriage 278, and the carriage 278 can be designed to move axially, to cause the axial movement of the lancet 250. Alternatively, the carriage 278 can be fixedly positioned, and the lancet 250 be designed to be axially moveable relative to the carriage 278.

Spring 282 is provided for biasing the lancet 250 to move in an axially outward direction, to engage tissue. A trigger member 284 is provided for maintaining the lancet 250 in its retracted position, until the user actuates the trigger 284, that releases the spring 282 to permit the lancet 250 to move axially outwardly, to thereby prick a tissue surface.

A depth gauge 286, including a camming surface for facilitating axial movement (not shown) is provided as a part of central portion 215 for enabling the user to adjust the extent of axial movement of the lancet 250, that permits the user to adjust the depth to which the penetrating tip 281 of the lancet 250 penetrates the tissue surface of the user. The depth gauge 286 includes pointer 288 (FIG. 9) that is reconcilable with numerical indicators 289 (FIG. 4) that provides an indication to the user of the relative depth to which the lancet 250 will penetrate. A gripping surface 292 is provided for permitting the user to rotate the cylindrical gauging wheel.

The second end body portion 216 also includes the test strip component 294 that is disposed generally at the distal end 296 of the second end body portion. The test strip component 294, test strip 298, receiver 300 and retainer 302 are virtually identical to test strip component 94, and does not need to be described again herein.

Testing device 210 also operates virtually identically to testing device 10, thereby eliminating the need to re-describe its method of operation.

The second alternate embodiment of the testing device 410 of the present invention is generally similar to testing device 10 insofar as it performs all of the functions of testing device 10. As is shown in FIGS. 15-20, device 210 utilizes a body 412 that includes a longitudinally extending second end body portion 416 that is attachable to and joinable with a lancet 450, cleansing member, and suction cap 454 containing end body portion 414 via a generally disk-shaped central portion 417. The testing device 410 includes a first, test strip component axis B, and a second lancet axis C, that is disposed at an outer angle to the test strip component axis B. The first end body portion 414 includes a radially outwardly facing ovaloid surface 420, a proximal end 424 and a distal end 426. A pair of support braces 425 help to securely connect the first end body portion 414 to the central portion 417.

An ovaloid-shaped cleansing member receiver 423 (FIG. 17) having a hollow central finger 429 is disposed within the interior of the proximal end 424 of the first end body portion 414, and is sized and configured for receiving a toroidal-shaped absorbent cleansing member 36. As will be described in more detail below, the central aperture and hollow finger of the cleansing member receiver are sized and positioned to permit lancet 450 (FIG. 18) to pass therethrough, so that when lancet 450 is in its fully extended position, the penetrating tip 481 of the lancet 450 will extend axially outwardly beyond the axially extending outwardly facing surface of the cleansing member. Of course, when the lancet 450 is in its retracted position, the penetrating tip 481 is disposed axially inwardly of the axially outwardly facing surface of the cleansing member, so that a person using the cleansing member to disinfect and clean a body tissue area prior to penetration does not stick himself with the lancet 450 while wiping down the tissue area.

Cap member 454 is ovaloid in cross section, and is hingedly coupled to the second end body portion 414 by a snap-type living hinge member 456. The cap member 454 is movable between an open position (as shown in FIGS. 15-17 and 20) wherein the longitudinal axis of the cap member 454 is generally parallel to the longitudinal axis C of the lancet 450, and a closed position wherein the cap member 454 is disposed generally co-axially with the lancet 450.

The distal end of the cap 454 is designed to mate with the proximal end of the first body portion 414, when the snap-type living hinge moves the cap member 454 to its closed position.

The living hinge members 456 are "snap-type" living hinge members that are designed to be spring-tensioned so that the cap 454 only finds a rest position when the cap 454 is in its open position as shown in FIG. 5, or in its closed position wherein the cap is disposed co-axially with the second body portion 414.

The proximal end of the cap member 454 includes a pressure cup 464 that is defined by a circumferential pressure inducing lip 466, and a cup-shaped interior. As with device 10, the placement of the circumferential pressure extending lip on a tissue area that surrounds a tissue site that has been penetrated by the tissue penetrator 481, along with the application of the moderate amount of axially directed force, has been surprisingly found by the Applicants to induce a flow of blood out of the penetrated site to enhance the volume of blood that is obtained from the penetrated site.

An axially movable tissue penetrator 472 (FIG. 19), that is movable between the retracted position, and an extended position includes a needle-like tissue penetrating lancet 450, that is coupled to a mounting member 478 The lancet 450 is movable between a retracted position wherein the penetrating tip 481 is disposed axially inwardly of the axially outer facing surface of the cleansing member so that when the user uses the cleansing member to cleans his finger (or forearm or other sticking site), he does not stick himself with the tip 481 of the lancet 450. The lancet 450 is also movable into an extended position, wherein it is moved axially outwardly, under the force of a biasing member, so that the penetrating tip 481 extends axially outwardly beyond the axially outer facing surface of the cleansing member, to prick the tissue site to cause bleeding therefrom.

A depth gauge 486, including a camming surface for facilitating axial movement (not shown) is provided as a part of central portion 415 for enabling the user to adjust the extent of axial movement of the lancet 450, that permits the user to adjust the depth to which the penetrating tip 481 of the lancet 450 penetrates the tissue surface of the user. The depth gauge 486 includes pointer 488 (FIG. 15) that is reconcilable with numerical indicators 489 that provides an indication to the user of the relative depth to which the lancet 450 will penetrate. A gripping edge 492 is provided for permitting the user to rotate the disk-shaped gauging wheel 479.

The second end body portion 416 also includes the test strip component 494 that is disposed generally at the distal end 496 of the second end body portion. The test strip component 494, test strip 498, receiver 500 and retainer 502 are virtually identical to test strip component 94, and do not need to be described again herein. Testing device 410 also operates virtually identically to testing device 10, thereby eliminating the need to re-describe its method of operation.

Although the invention has been described with reference to the currently perceived best mode of practicing the invention, it will be appreciated by those skilled in the art the variation and modifications exist which are encompassed within the spirit of the invention.

What is claimed is:

1. A single use, disposable body fluid testing device for use with a testing meter, the device comprising:
   a disposable body member, the body member being a separate component from the testing meter,
   an axially moveable tissue penetrator carried by the body member, the tissue penetrator including a depth adjustor for enabling a user to adjust the extent of axial movement of the tissue penetrator
   a test strip holder carried by the body member, and
   a test strip carried on the disposable body member by the test strip holder, the test strip being capable of receiving a body fluid thereon and processing the body fluid into a form suitable for yielding test results relating to the content of the body fluid,
   wherein the test strip holder includes a test strip receiver for receiving the test strip, and a test strip retainer for retaining the test strip on the test strip receiver, wherein the test strip, while being carried on the disposable body member, is lifted relative to the test strip holder by the meter when the test strip is engaged with a testing meter, and
   wherein the body member and each of the tissue penetrator, test strip holder and test strip carried on the body member are designed for a single use and for disposal as a unit without disassembly from each other or from other components.

2. The testing device of claim 1, further comprising a cleansing member carried by the body member for cleansing a tissue area to be penetrated by the tissue penetrator, and wherein at least one of the test strip receiver and test strip retainer are positioned in a spaced relation from the test strip for facilitating engagement of the test strip with a testing meter, to permit the testing meter to impart a the lifting movement to the test strip, and the testing meter comprises at least one of a photometric and electro-sensimetric detector.

3. The testing device of claim 1, further comprising a pressure inducing member carried by the body member, the pressure inducing member being capable of inducing pressure on a tissue site penetrated by the penetrating member for inducing an enhanced flow of fluid from the penetrated tissue site.

4. The testing device of claim 3 wherein the test strip holder includes a pair of complimentary ramping surfaces formed on the holder for facilitating engagement of the test strip component with the testing meter for permitting the testing meter to lift the test strip as it is inserted into the meter.

5. The testing device of claim 3 wherein the body member includes a first end, a second end, and a hand engaging surface disposed between the first and second ends.

6. The testing device of claim 5 wherein the tissue penetrator is axially movable between a retracted and an extended position, and includes a biasing member for biasing the tissue penetrator into the extended position.

7. The testing device of claim 6 wherein the tissue penetrator includes an actuator for retaining the tissue penetrator in the retracted position, and upon activation by a user, for releasing the tissue penetrator to permit the tissue penetrator to move into the extended position.

8. The testing device of claim 6 further comprising a cleansing member carried by the body member for cleansing a body tissue area to be penetrated by the penetrator wherein the cleansing member is disposed adjacent to the first end of the body member, and includes a cleanser containing pad for cleaning the tissue area to be penetrated by the tissue penetrator.

9. The testing device of claim 1 wherein the tissue penetrator is axially movable between a retracted and an extended position and includes a biasing member for biasing the tissue penetrator into the extended position, the tissue penetrator further including an actuator for retaining the tissue penetrator in the retracted position, and releasing the tissue penetrator upon activation by a user, to move into the extended position.

10. The testing device of claim 9, further comprising a cleansing member carried by the body member and having an axially outer cleansing surface for cleansing a body tissue area to be penetrated by the tissue penetrator, wherein the tissue penetrator includes a penetrating tip, the penetrating tip being disposed axially inwardly of the axially outer cleansing surface of the cleansing member when the tissue penetrator is in the retracted position to prevent engagement of the penetrating tip with body tissue when the cleansing surface is engaging the tissue.

11. The testing device of claim 1 further comprising a single use disposable cleansing member carried by the body member and disposed adjacent to the tissue penetrator for cleansing a tissue site immediately prior to the site being penetrated by the tissue penetrator, the cleansing member being coupled to the body member for disposal with the body member as a unit.

12. The testing device of claim 1 wherein the test strip holder includes a window for permitting the user to view the test strip to determine whether sufficient body fluid has been applied to the test strip to give a precise and accurate result.

13. The testing device of claim 1 wherein the test strip includes a reaction area and a reagent capable of producing a color upon reaction with the body fluid, whereby the color provides an indication of the test results.

14. A single use, disposable body fluid testing device comprising:
   a disposable body member having a first end and a second end,
   an axially moveable tissue penetrator carried by the body member adjacent to the first end of the body member, the tissue penetrator including a depth adjuster for enabling a user to adjust the extent of axial movement of the tissue penetrator,
   a test strip holder carried by the body member adjacent to the second end of the body member,
   a test strip carried on the disposable body member by the test strip holder adjacent to the second end of the body member, the test strip being capable of receiving a body fluid thereon and processing the body fluid into a form suitable for yielding test results relating to the content of the body fluid, and
   a single use disposable cleansing member carried by the body member, the cleansing member being coupled to the body member for disposal with the body member as a unit and
   wherein the test strip holder includes a pair of complimentary ramping surfaces formed on the holder, the ramping surfaces being engageable with a testing meter so that while the test strip is carried by the test strip holder, the testing meter lifts the test strip relative to the test strip holder as the testing meter is inserted into the meter for better fitting of the test strip by the testing meter.

15. The testing device of claim 14 further comprising a pressure inducing member carried by the body member adjacent to the first end of the body member, the pressure inducing member being capable of inducing pressure on a tissue site penetrated by the penetrating member for inducing an enhanced flow of fluid from the penetrated tissue site, further comprising a depth gauge coupled to the depth adjuster, the depth gauge including a pointer, that is reconcilable with a gauging surface to provide an indication of relative depth to which the tissue penetrator will penetrate.

16. A single use, disposable body fluid testing device comprising:
a body member having a first end and a second end;
an axially moveable tissue penetrator carried by the body member adjacent to the first end of the body member, the tissue penetrator including a depth adjustor for enabling a user to adjust the extent of axial movement of the tissue penetrator,
a test strip holder carried by the body member,
a test strip carried by the test strip holder adjacent to the second end of the body member, the test strip being capable of receiving a body fluid thereon and processing the body fluid into a form suitable for yielding test results relating to the content of the body fluid, wherein the test strip holder includes a window adjacent to the test strip for permitting the user to view the test strip to determine whether sufficient body fluid has been applied to the test strip to give a precise and accurate result,
wherein the test strip holder includes a test strip receiver for receiving the test strip, the test strip, while being carried by the test strip holder, is lifted by the testing meter relative to the test strip holder when the test strip is engaged with a testing meter.

17. A body fluid testing device for use with a testing meter, the device comprising:
a single use disposable body member, the body member not being formed as a part of or coupled to the meter, the body member having a first end and a second end,
an axially moveable tissue penetrator carried by the body member, the tissue penetrator including a depth adjustor for enabling a user to adjust the extent of axial movement of the tissue penetrator,
a test strip holder carried on the body member,
a test strip carried on the disposable body member by the test strip holder, the test strip being capable of receiving a body fluid thereon and processing the body fluid into a form suitable for yielding test results relating to the content of the body fluid, and
a cleansing member carried by the body member, wherein the test strip holder includes a test strip receiver for receiving the test strip, a test strip retainer for retaining the test strip on the test strip receiver, and a hinge for hingedly coupling the test strip receiver to the test strip retainer, and wherein at least one of the test strip receiver and test strip retainer are positioned in a spaced relation from the test strip for facilitating engagement of the test strip with a testing meter, wherein the test strip, while being carried on the disposable body member, is lifted relative to the test strip holder when the test strip is engaged with a testing meter.

18. The testing device of claim 17 further comprising a pressure inducing member carried by the body member adjacent to the first end of the body member, the pressure inducing member being capable of inducing pressure on a tissue site penetrated by the penetrating member for inducing an enhanced flow of fluid from the penetrated tissue site.

19. The testing device of claim 4 wherein the depth gauge includes a pointer that is reconcilable with a gauging surface to provide an indication to the user of the relative depth to which the tissue penetrator will penetrate.

20. The testing device of claim 19 wherein the depth adjuster includes a camming surface for facilitating axial movement, and wherein the gauge include a gauging wheel rotatable by a user to vary the depth to which the tissue penetrator will extend.

21. The testing device of claim 16 further comprising a test strip retainer for retaining the test strip on the test strip receiver, and wherein at least one of the test strip receiver and test strip retainer are positioned in a spaced relation from the test strip for facilitating engagement of the test strip with a testing meter, so that the testing meter engages the test strip to lift the test strip during the time that the test strip enters the testing meter.

* * * * *